US010433549B2

(12) United States Patent
O'Sullivan et al.

(10) Patent No.: US 10,433,549 B2
(45) Date of Patent: *Oct. 8, 2019

(54) NON-NEMATICIDAL COMPOSITION AND USE THEREOF

(71) Applicant: BIOATLANTIS LTD, Tralee, County Kerry (IE)

(72) Inventors: John T. O'Sullivan, Tralee (IE); Kieran Guinan, Tralee (IE); Sujeeth Neerakkal, Tralee (IE)

(73) Assignee: BioAtlantis Limited, Tralee, County Kerry (IE)

( * ) Notice: Subject to any disclaimer, the term of this patent is extended or adjusted under 35 U.S.C. 154(b) by 269 days.

This patent is subject to a terminal disclaimer.

(21) Appl. No.: 14/775,206

(22) PCT Filed: Mar. 20, 2014

(86) PCT No.: PCT/EP2014/055650
§ 371 (c)(1),
(2) Date: Sep. 11, 2015

(87) PCT Pub. No.: WO2014/147199
PCT Pub. Date: Sep. 25, 2014

(65) Prior Publication Data
US 2016/0029627 A1 Feb. 4, 2016

(30) Foreign Application Priority Data
Mar. 20, 2013 (IE) .................................. 2013/0100

(51) Int. Cl.
A01N 43/16 (2006.01)
A01N 65/03 (2009.01)
A01N 65/00 (2009.01)
A01N 31/02 (2006.01)

(52) U.S. Cl.
CPC ............. A01N 43/16 (2013.01); A01N 31/02 (2013.01); A01N 65/00 (2013.01); A01N 65/03 (2013.01); Y02A 50/351 (2018.01)

(58) Field of Classification Search
None
See application file for complete search history.

(56) References Cited

U.S. PATENT DOCUMENTS

| | | | |
|---|---|---|---|
| 6,387,847 B1 * | 5/2002 | Yvin ...................... | A01N 43/16 504/117 |
| 6,582,961 B1 | 6/2003 | Moon et al. | |
| 7,927,635 B2 | 4/2011 | Moon | |
| 2002/0004458 A1 | 1/2002 | Graham et al. | |
| 2007/0261139 A1 | 11/2007 | Singh | |
| 2009/0104222 A1 * | 4/2009 | Freund ................... | A01N 43/16 424/195.17 |
| 2009/0148414 A1 | 6/2009 | O'Doherty et al. | |
| 2010/0040656 A1 * | 2/2010 | Franklin ................ | A01N 25/26 424/405 |
| 2019/0021324 A1 * | 1/2019 | O'Sullivan ............ | A01N 43/16 |

FOREIGN PATENT DOCUMENTS

| | | |
|---|---|---|
| CN | 102125064 B | 4/2013 |
| KR | 10-0773148 B1 | 11/2007 |

OTHER PUBLICATIONS

Crouch et al., "Evidence for the presence of plant growth regulators in commercial seaweed products", Plant Growth Regulation 13: 21-29 (1993).*
Sultana et al, "Comparative Efficacy of a red alga Solieria robusta, chemical fertilizers and pesticides in managing the root diseases and growth of soybean", Pak J Bot 43: 1-6 (2011).*
Sultana et al., "Effect of brown seaweeds and pesticides on root rotting fungi and root-knot nematode infecting tomato roots", J Applied Botany and Food Quality 83: 50-53 (2009).*
"Minimizing Pesticide Risk to Bees in Fruit Crops", Michigan State University Extension bulletin E3245.*
Eilperin, "In a surprise move, EPA bans carbofuran residue on food", Washington Post, Jul. 25, 2008.*
Crouch et al., "Evidence for the presence of plant growth regulators in commercial seaweed products", Plant Growth Regulation 13: 21-29 (1993) (Year: 1993).*
Eilperin, "In a surprise move, EPA bans carbofuran residue on food", Washington Post, Jul. 25, 2008 (Year: 2008).*
Sultana et al., "Comparative Efficacy of a red alga Solieria robusta, chemical fertilizers and pesticides in managing the root diseases and growth of soybean", Pak J Bot 43: 1-6 (2011) (Year: 2011).*
Sultana et al., "Effect of brown seaweeds and pesticides on root rotting fungi and root-knot nematode infecting tomato roots", J Applied Botany and Food Quality 83: 50-53 (2009) (Year: 2009).*
Michigan State University Extension bulletin E3245 (Year: 2017).*
O. Klarzynski, et al.; "Linear β- 1,3 glucans are elicitors of defence responses in Tobacco"; Nov. 2000; Plant Physiology; vol. 124, pp. 1027-1038.
J.A. Lamondia; "Management of lesion nematodes and potato early dying with rotation crops"; 2006; Journal of Nematolgy; vol. 38; No. 4; pp. 442-448.

(Continued)

Primary Examiner — Abigail Vanhorn
(74) Attorney, Agent, or Firm — Studebaker & Brackett PC

(57) ABSTRACT

A non-nematicidal composition comprises at least one glucan and/or at least one fucan which act individually or synergistically with mannitol to reduce losses in crop yield and marketable grade caused by the infestation of growth media with plant pathogenic nematodes, to levels equivalent to those achieved with commercial nematicides, but without posing a risk to the ecosystem or user. In some cases the composition comprises at least one glucan, at least one fucan and at least one mannitol which may be in a weight/weight ratio of approximately 1:2:3 of at least one glucan:at least one fucan:at least one mannitol or between approximately 1:1:1 to 1:1:3 of at least one glucan:at least one fucan:at least one mannitol.

24 Claims, 3 Drawing Sheets

(56) References Cited

OTHER PUBLICATIONS

S.G. Leonard, et al.; "Effect of dietary seaweed extracts and fish oil supplementation in sows on performance, intestinal microflora, intestinal morphology, volatile fatty acid concentrations and immune status of weaned pigs"; 2011; British Journal of Nutrition; vol. 105; pp. 549-560.
S.G. Leonard, et al.; "Effects of dietary seaweed extract supplementation in sows and post-weaned pigs on performance, intestinal morphology, intestinal microflora and immune status"; British Journal of Nutrition; 2011; vol. 106; No. 5; pp. 688-699.
Y. Li et al.; "Effect of methanol on soybean photosynthesis and chlorophyll"; Journal of Plant Nutrition; 1995; vol. 18; No.9; pp. 1875-1880.
M. Loison; "Alternative control of nematodes makes its first steps"; 2012; Plant Protection Corner; Issue 3 Sep./Oct., p. 26-30; New Ag International. http://www.newaginternational.com.
L. London et al.; "Effects of long-term organophosphate exposures on neurological symptoms, vibration sense and tremor among South African farm workers"; 1998; Scandinavian Journal of Work Environment & Health; vol. 24; No. 1; pp. 18-29. http://www.sjweh.fi.
S.J. Mackenzie, et al.; "Neuropsychological and psychiatric functioning in sheep farmers exposed to low levels of organophosphate pesticides"; Neurotoxicology and Teratology; 2010; vol. 32; pp. 452-459.
P. Magnelli, et al.; "A refinied method for the determination of *Saccharomyces cerevisiae* cell wall composition and beta-1,6-gulca fine structure"; 2002; Analytical Biochemistry; vol. 301; pp. 136-150(Abstract only).
D.C. Mahan; "Efficacy of Dried Whey and Its Lactalbumin and Lactose Components at Two Dietary Lysine Levels on Postweaging Pig Performance and Nitrogen Balance"; Journal of Animal Science; 1992; vol. 70; pp. 2182-2187.
T.J. Martin, et al.; "Management of the potato cyst nematode (*Globodera pallida*) with bio-fumigants/stimulants"; Commun Agric Appl Biol Sci; 2007; vol. 72; No. 3; pp. 671-675(Abstract only). http://www.ncbi.nlh.nih.gov/pubmed/18399503.
P. McDonnell, et al.; "The effect of dietary laminarin and fucoidan in the diet of the weanling piglet on performance, selected fecal microbial populations and volatile fatty acid concentrations"; Animal; 2010; vol. 4; pp. 579-585.
T.K. Means; "Fungal pathogen recognition by scavenger receptors in nematodes and mammals"; 2010; Virulence; vol. 1; Issue1; pp. 37-41.
D.A. Neher; "Ecology of plant and free-living nematodes in natural and agricultural soil"; Annu. Rev. Phytopathol; 2010; vol. 48; pp. 371-394.
J.W. Noling; "Movement and Toxicity of Nematicides in the Plant Root Zone"; 2002; Institute of Food and Agricultural Sciences Fact Sheet ENY-041, University of Florida Department of Entomology and Nematology, Florida Cooperative Extension Service. Online: http://edis.ifas.ufl.edu/pdffiles/NG/NG00200.pdf (accessed Jan. 10, 2013).
A.M. Nonomura, et al.; "The path of carbon in photosynthesis: improved crop yields with methanol"; Oct. 1992; Proc. Natl. Acad. Sci. USA; vol. 89; pp. 9794-9798.
D. Nordmeyer, et al.; "Effect of ethoprop, carbofuran, and aldicarb on flue-cured tobacco infected with three species of Meloidogyne"; 1982; Nematropica; vol. 12; No. 2; pp. 199-204.
M. Novak, et al.; "Glucans as Biological Response Modifiers"; Endocrine, Metabolic & Immunete Disorders-Drug Targets; 2009; vol. 9. pp. 67-75.
H. Okada, et al.; "Application of diversity indices and ecological indices to evaluate nematode community changes after soil fumigation"; Dec. 2004; Japanese Journal of Nematology; vol. 34; No. 2; pp. 89-98.
M.A. O'Malley, et al.; "Illness Associated with Exposure to Methyl Bromide—Fumigated Produce—California, 2010", Jul. 15, 2011; MMWR; vol. 60; No. 27; pp. 923-926.

C.E. Pankhurst, et al.; "Effects of biocides and rotation breaks on soil organisms associated with the poor early growth of sugarcane in continuous monoculture"; Plant and Soil; 2005; vol. 268; pp. 255-269.
S. Paracer, et al.; "Effective use of marine algal products in the management of plant-parasitic nematodes"; Journal of Nematology; 1987; vol. 19; No. 22 ; pp. 194-200.
G.S. Rahi, et al.; "Ethoprop Depletion from Soil as Influenced by Simulated Rainfall"; Journal of Nematology; 1992; vol. 24; No. 4S; pp. 642-647.
V. Ramamoorthy, et al.; "Induction of systemic resistance by plant growth promoting rhizobacteria in crop plants against pests and diseases"; 2001; Crop Protection; vol. 20; No. 1; pp. 1-11.
S. Read, et al.; "Analysis of the structural heterogeneity of laminarin by electrospray-ionisation-mass sectrometry"; Carbohydrate Research; 1996; vol. 281; pp. 187-210.
D. Riou, et al.; "Antitumor and antiproliferative effects of a fucan extracted from ascophyllum nodosum against a non-small-cell bronchopulmonary carcinoma line"; Anticancer Research; 1996; vol. 16; No. 3A; pp. 1213-1218(Abstract only).
J.R. Reeve, et al; "Effects of soil type and farm management on soil ecological functional genes and microbial activities"; The ISME Journal; 2010; vol. 4; pp. 1099-1107; PMID: 20376100.
P. Reilly, et al.; "The effects of seaweed extract inclusion on gut morphology, selected intestinal micobiota, nutrient digestibility, volatile fatty acid concentrations and he immune status of the waned pig" Animal; 2008; vol. 2; No. 10; pp. 1465-1473.
J.R. Rich, et al.; "Population Development and Pathogenicity of Meloidogyne javanica on Flue-cured Tobacco as influenced by ethoprop and DD"; Journal of Nematology; 1984; vol. 16; No. 3; pp. 240-245.
M. Rivgas-San Vicente, et al.; "Salicylic acid beyond defence: its role in plant growth and development"; Journal of Experimental Botany; 2011; vol. 6; No. 10; pp. 321-3338.
W.A. Rohde, et al.; "Influence of Climate and Cropping Patterns on the Efficacy of Ethoprop, Methyl Bromide, and DD-MENCS for Control of Root-knot Nematodes"; Journal of Nematology; 1980; vol. 12, No. 1; pp. 33-39.
D.S. Rohlman, et al.; "Correlating neurobehavioral performance with biomarkers of organophosphorus pesticide exposure"; NeuroToxicology; 2011; vol. 32; pp. 268-276.
L. Roldan-Tapia, et al.; "Neuropsychological effects of long-term exposure to organophosphate pesticides"; Neurotoxicology and Teratology; 2005; vol. 27; pp. 259-266.
L. Rosenstock, et al.; "Chronic central nervous system effects of acute organophosphate pesticide intoxication"; The pesticide Health Effects Study Group; Lancet; Jul. 27, 1991; vol. 338; pp. 223-227.
O.R. Russo, et al.; "The use of organic biostimulants to help low input sustainable agriculture"; Journal of Sustainable Agriculture; 1990; vol. 1; No. 2; pp. 19-42.
S. Sanchez-Moreno, et al.; Nematodes as indicators of fumigant effects on soil food webs in strawberry crops in southern Spain; Ecological Indicators; 2010; vol. 10; pp. 148-156.
S. Sattler, et al.; "Evolution of the C-Type Lectin-Like Receptor Genes of the DECTIN-1 Cluster in the NK Gene Complex";37 Scientific World Journal; vol. 2012; Article ID 931386; 11pages.
A.G. Smith, et al.; "The effects of laminarin derived from Laminaria digitata on measurements of gut health: selected bacterial populations, intestinal fermentation, mucin gene expression and cytokine gene expression in the pig"; British Journal of Nutrition; 2011; vol. 105; pp. 669-677.
L. Stallones, et al.; "Pesticide poisoning and depressive symptoms among farm residents"; Ann Epidemiol; 2002; vol. 12; No. 6; pp. 389-394.
S.E. Starks, et al.; "High pesticide exposure events and central nervous system function among pesticide applicators in the Agricultural Health Study"; Int Arch Occup Environ Health; 2012; vol. 85; pp. 505-515. DOI: 10.1007/s00420-011-0694-8.
K. Steenland, et al.; "Chronic Neurological Sequelae to Organophosphate Pesticide Poisoning"; American Journal of Public Health; May 1994; vol. 84; No. 5; pp. 731-736.

(56) References Cited

OTHER PUBLICATIONS

W.A. Stirk, et al.; "Comparison of cytokinin- and auxin-like activity in some commercially used seaweed extracts"; Journal of Applied Phycology; 1997; vol. 8; Issue 6; pp. 503-508.
A.V. Sturz, et al.; "Effects of fosthiazate and aldicarb on populations of plant-growth-promoting bacteria, root-lesion nematodes and bacteria-feeding nematodes in the root zone of potatoes"; Plant Pathology; 1999; vol. 48; pp. 26-32.
V. Sultana, et al.; "Comparative efficacy of a red alga *Solieria robusta*, chemical fertilizers and pesticides in managing the root diseases and growth of soybean"; Pak. J. Bot.; 2011; vol. 43; No. 1; pp. 1-6.
P.G. Tillman, et al.; "Comparison of susceptibility of pest Euschistus serous and predator Podisus maculiventris (Heteroptera: Pentatomidae) to selected insecticides"; Journal of Economic Entomology; Jun. 2004; vol. 97; No. 3; pp. 800-806.
A.C.Triantaphyllou, et al.; "Environmentally controlled sex expression in Meloidodera fioridensis"; Journal of Nematology; Jul. 1973; vol. 5; No. 3; pp. 181-185.
A.C.Triantaphyllou; "Environmental sex differentiation of nematodes in relation to pest management"; Annu. Rev. Phytopathol; 1973; vol. 11; pp. 441-462.
D.L. Trudgill, et al.; The effect of resistant solanaceous plants on the sex ratio of Heterodera rostochiensis and the use of the sex ratio to assess the frequency and genetic constitution of pathotypes; Ann. Appl. Biol.; 1967; vol. 60; pp. 421-428.
UNEP(United Nations Environment Programme); "Effects of Trade Liberalization on Agriculture in Lebanon: With Special Focus on Products Where Methyl Bromide Is Used"; 2005; Division of Technology.
T.T.M. Vandekerckhove, et al.; "Occurrence of novel verrucomicrobial species, endosymbiotic and associated with parthenogenesis in Xiphinema americanum- group species (nematoda, Longidoridae)"; International Journal of Systematic and Evolutionary Microbiology; 2000; vol. 50; pp. 2197-2205.
W.K. Anger; "Neurobehavioural tests and systems to assess neurotoxic exposures in the workplace and community"; Occup Environ Med; vol. 60; No. 7; 2003; pp. 531-538.
J. Ara, et al.; "Biological activity of Spatoglossum asperum: a brown alga"; 2005; Phytotherapy Research; vol. 19; pp. 618-623.
R.D. Bardgett, et al.;"Below-ground herbivory promotes soil nutrient transfer and root growth in grassland"; 1999; Ecology Letters; vol. 2; pp. 357-360.
P.G. Bardin, et al.; "Organophosphate and carbamate poisoning"; 1994; Arch Intern Med; vol. 154, No. 13; pp. 1433-1441.
N.L. Bell, et al.; "Non-target effects of a carbamate and the proteins avidin and aprotinin on in vitro development of a bacterial feeding nematode"; Sep. 2006; Soil Biology and Biochemistry; vol. 38; Issue 9; pp. 2816-2822.
D.M. Bird, et al.; "Are roots special? Nematodes have their say"; 2003; Physiological and Molecular Plant Pathology; vol. 62; pp. 115-123.
C. Blondin, et al.; "Relationships between chemical characteristics and anticomplementary activity of fucans"; Mar. 1996; Biomaterials; vol. 17; No. 6; pp. 597-603.
G. Bocquene, et al.; "Pesticide contamination of the coastline of Martinique"; 2005; Marine Pollution Bulletin; vol. 51; pp. 612-619.
M. Boran, et al; "Acute toxicity of carbaryl, methiocarb, and carbosulfan to the rainbow trout Oncorhynchus mykiss and guppy (*Poecilia reticulata*)"; 2007; Turk J. Vet. Anim. Sci.; vol. 31; No. 1; pp. 39-45.
B.T. Bowman; "Mobility and persistence of metachlor and aldicarb in field lysimeters"; 1988; Journal of Environmental Quality; vol. 17; No. 4; pp. 689-694.
R.J. Bushway; "High-performance liquid chromatographic determination of carbaryl and 1-naphtol at residue levels in various water sources by direct injection and trace enrichment"; 1981; Journal of Chromatography; vol. 211; pp. 135-143.

R.J. Bushway, et al.; "Atrazine, Alachlor and Carbofuran contamination of well water in Central Maine"; 1992; Bull. Environ. Contam. Toxicol.; vol. 49; pp. 1-9.
R.G. Carneiro, et al.; "Uptake and translocation of nitrogen, phosphorus and calcium in soybean infected with Meloidogyne incognita and M. javanica"; 2002; Fitopatol. Bras.; vol. 27; No. 2; pp. 141-150.
P. Castagnone-Sereno; "Genetic variability and adaptive evolution in parthenogenetic root-knot nematodes"; 2006; Heredity; vol. 96; pp. 282-289.
X.Y. Cheng, et al.; "Metagenomic analysis of the pinewood nematode microbiome reveals a symbiotic relationship critical for xenobiotics egradation"; 2013; Scientific Reports; vol. 3,1869; pp. 1-10.
B. Chinnasri, et al.; "Effects of Inducers of Systemic Acquired Resistance on Reproduction of Meloidogyne javanica and Rotylenchulus reniformis in Pineapple"; Sep. 2006; Journal of Nematology; vol. 38; No. 3; pp. 319-325.
S. Chiron, et al.; "Determination of pesticides in drinking water by on-line solid-phase disk extraction followed by various liquid chromatographic systems"; 1993; Journal of Chromatography; vol. 645; pp. 125-134.
S. Chiron, et al.; "Application of on-line solid-phase extraction followed by liquid chromatography thermospray mass spectrometry to the determination of pesticides in environmental waters"; 1994; Journal of Chromatography A; vol. 665; pp. 295-305.
D.J. Chitwood; "Nematicides" in Encyclopedia of Agrochemicals(3); 2003; pp. 1104-1115; John Wiley & Sons, New York, NY.
K. Chojnacka, et al; "Biologically Active Compounds in Seaweed Extracts—the Prospects for the Application"; 2012; The Open Conference Proceedings Journal; vol. 3; Suppl 1-M4; pp. 20-28.
M. Cone; "Toxic Pesticide Banned after Decades of Use: Scientific American"; Aug. 18, 2010; Scientific American.
S.E. Cowgill, et al.; "The effect of transgenic nematode resistance on non-target organisms in the potato rhizosphere"; 2002; Journal of Applied Ecology; vol. 39; pp. 915-923.
I.J. Crouch, et al., "Effect of seaweed concentrate from Ecklonia maxima (Osbeck) Papenfuss on Meloidogyne incognita infestation on tomato"; 1993; Journal of Applied Phycology; vol. 5; pp. 37-43.
I.J. Crouch, et al.; "Evidence for the presence of plant growth regulators in commercial seaweed products"; 1993; Plant Growth Regulation; vol. 13; pp. 21-29.
GB. De Deyn, et al.; "Plant community development is affected by nutrients and soil biota"; 2004; Journal of Ecology; vol. 92; pp. 824-834.
D. De Waele, et al.; "Influence of seaweed concentrate on the reproduction of Pratylenchus zeae (Nematoda) on maize"; 1988; Nematologica; E.J. Brill, Leiden; vol. 34; pp. 71-77.
T. S. S. Dikshith, et al.; "Residues of 1-naphtol in soil and water samples in and around Bhopal, India"; 1990; Bull. Environ. Contam. Toxicol.; vol. 44; pp. 87-91;.
"DuPont™ Vydate® insecticide/nematicide. Protect your crops against damage from insects, mites and nematodes"; Technical Bulletin; Source: http://www2.dupont.com/Production_Agriculture/en _US/assets/downloads/pdfs/H-95402.pdf; accessed: 11_01_2013.
A. Dursun, et al.; "Effects of different priming treatments and priming durations on germination percentage of parsley (*Petroselinum crispum* L.) seeds"; 2012; Agricultural Sciences; vol. 1; No. 1; pp. 17-23.
"Pesticide Residues Monitoring Programme for Quarter 4 2011" [Online]; Available at http://www.pesticides.gov.uk/Resources/CRD/PRiF/Q4_2011_report.pdf (Accessed Nov. 1, 2013); ECPRF Expert Committee on Pesticide Residues in Food; Jul. 2012.
C. Ellenby; "Environmental determination of the sex ratio of a plant-parasitic nematode"; Nov. 1954;Nature; vol. 174; pp. 1016-1017.
"Agreement to Terminate All Uses of Aldicarb"; US EPA; 2010; Source: U. S. Environmental Protection Agency's Office of Pesticide Programs, EPA Pesticide Program; http://www.epa.gov/oppsrrd1/REDs/factsheets/aldicarb_fs.html.
"What is a pesticide?"; US EPA; 2013; Source: http://www.epa.gov/pesticides/about/index.htm [accessed Jan. 10, 2013].

(56) References Cited

OTHER PUBLICATIONS

"Directive 2009/128/EC of the European Parliament and of the Council of Oct. 21, 2009 establishing a Framework or Community Action to Achieve the Sustainable Use of Pesticides (Text with EEA relevance)"; Official Journal of the European Union; Nov. 24, 2009; L 309; pp. 71-82; European Commission (EU).

"Regulation (EC) No. 178/2002 of the European Parliament and of the Council of Jan. 28, 2002, laying down the general principles and requirements of food law, establishing the European Food Safety Authority and laying down procedures in matters of food safety"; Official Journal of the European Union; Feb. 1, 2002; L 31; pp. 1-24; European Commission (EU).

"Pesticide residues in food—2002"; Report of the Joint Meeting of the FAO Panel of Experts on Pesticide Residues in Food and the Environment and the WHO Core Assessment Group on Pesticide Residues; Sep. 16-25, 2002; pp. 198-213; FAO/WHO; Rome, Italy.

T.M. Farahat, et al.; "Neurobehavioral effects among workers occupationally exposed to organophosphate pesticides"; 2003; Occup Environ Med; vol. 60; pp. 179-286.

B.C. Featonby-Smith, et al.; "The effect of seaweed concentrate on the growth of tomato plants in nematode infested soil"; Scientia Horticulturae; 1983; vol. 20; pp. 137-146; Elsevier Science Puiblishers.

M.P. Garcia De Llasera, et al.; "Presence of carbamate pesticides in environmental waters from the northwest of Mexico: Determination by liquid chromatography"; Wat.Res.; 2001; pp. 1933-1940; vol. 35; No. 8; Pergamon.

R. Garcia-M, et al.; "Efficacy of selected fumigant and nonfumigant nematicides to control Meloidogyne javanica in Florida tobacco"; 1983; Nematropica; vol. 13; No. 2; pp. 125-134.

S.R.Gowen; "Chemical control of nematodes: efficiency and side-effects"; in Plant Nematode Problems and their control in the Near East Region (FAO Plant Production and Protection Paper—144); 1992.

F. Grundler, et al.; "Influence of changes in the nurse cell system (syncytium) on sex determination and development of the cyst nematode Heterodera schachtii: Total amounts of proteins and amino acids"; 1991; Physiology and Biochemistry; vol. 81; No. 1; pp. 70-74; Phytopathology; The American Phytopathological Society.

N. Hamamouch, et al.; "The interaction of the novel 30C02 cyst nematode effector protein with a plant β-1,3-endoglucanase may suppress host defence to promote parasitism"; Journal of Experimental Botany; Mar. 2012; vol. 63; No. 10; pp. 3683-3695.

R.S. Hussey; "Disease-inducing secretions of plant-parasitic nematodes"; 1989; Annu. Rev. Phytopathol; vol. 27; pp. 123-141.

R.E. Ingham, et al.; "Interactions of bacteria, fungi, and their nematode grazers: effects on nutrient cycling and plant growth": Mar. 1985; Ecological Monographs; vol. 55; pp. 119-140; Ecological Society of America.

A.M. Ibekwe; "Effects of Fumigants on Non-Target Organisms in Soils"; 2004; Advances in Agronomy; vol. 83; pp. 1-35.

T. Jenkins, et al.; "Are the reductions in nematode attack on plants treated with seaweed extracts the result of stimulation of the formaldehyde cycle?"; 1998; Acta Biologica Hungarica; vol. 49; pp. 421-427(Abstract only). http://europepmc.org/abstract/med/10526988.

T. Kikuchi, et al.; "Molecular and biochemical characterization of an endo-beta-1,3-glucanase from the pinewood nematode Bursaphelenchus xylophilus acquired by horizontal gene transfer from bacteria"; 2005; Biochem. J.; vol. 389; pp. 117-125; Biochemical Society.

J. Kimpinski, et. al.; "Nematicides increase grain yields in spring wheat cultivars and suppress plant-parasitic and bacterial-feeding nematodes"; 2005; Journal of Nematology; vol. 37; No. 4; pp. 473-476.

T. L. Kirkpatrick, et al.; "Interaction of Meloidogyne incognita and water stress in two cotton cultivars"; 1991; Journal of Nematology; vol. 23; No. 4; pp. 462-467.

International Search Report for PCT/EP2014/055650 dated Aug. 27, 2014.

Written Opinion for PCT/EP2014/055650 dated Aug. 27, 2014.

Khan et al.; Seaweed Extracts as Biostimulants of Plant Growth and Development; Journal of Plant Growth Regulation; Springer Science+Business Media, LLC; vol. 28, No. 4; 2009; pp. 286-399.

S. Wada, et al.; "Effects of the nematicide imicyafos on soil nematode community structure and damage to radish mused by Pratylenchus penetrans"; Journal of Nematology; Mar. 2011; vol. 43; No. 1; pp. 1-6. PMID: 22791909.

C. Wesseling, et al.; Long-term neurobehavioral effects of mild poisonings with organophosphate and n-methyl carbamate pesticides among banana workers: Int J Occup Environ Health; 2002; vol. 8; No. 1; pp. 27-34.

A.G. Whitehead, et al.; "Control of potato cyst-nematode, Globodera rostochiensis, and root-knot nematode, Meloidogyne incognita, by organosphosphorus, carbamate, benzimidazole and other compounds"; Annals of Applied Biology; 1985; vol. 106; pp. 489-498.

V.M. Williamson, et al.; "Nematode pathogenesis and resistance in plants"; The Plant Cell; Oct. 1996; vol. 8; pp. 1735-1745.

E. Wolski, et al.; "Cell wall alpha-1,3-glucans from a biocontrol isolate of Rhizoctonia: immunocytolocalization and relationship with alpha-glucanase activity from potato sprouts"; Mycological Research III; 2007; pp. 976-984.

Y. Wu; et al.; "Suppression of fecundity of the root-knot nematode, Meloidogyne javanica, in monoxenic cultures of *Arabidopsis thaliana* treated with an alkaline extract of Ascophyllum nodosum"; Journal of Applied Phycology; 1998; vol. 10; pp. 91-94.

Y. Wu, et al.; "The role of betaines in alkaline extracts of Ascophyllum nodosum in the reduction of Meloidogyne avanica and M. incognita infestations of tomato plants"; Fundam. Appl. Nematol; 1997; vol. 20; No. 2; pp. 99-102.

C.A. Whapham, et al.; "The role of seaweed extracts, Ascophyllum nodosum, in the reduction in fecundity of Meloidogyne javanica"; Fundam. Appl. Nematol; 1994; vol. 17; No. 2 ; pp. 181-183.

E.A. Wolski, et al.; "A novel α-1, 3-glucan elicits plant defense responses in potato and induces protection against Rhizoctonia solani AG-3 and *Fusarium solani* f. sp. *eumartii*"; Physiological and Molecular Plant Pathology; 2006; vol. 69; pp. 93-103.

G.W. Yeates; "Effects of 2 nematicides on biological activity in a Typic Haplaquoll at Castlepoint 2. Nematodes"; New Zealand Journal of Agricultural Research; 1985; vol. 28; pp. 141-150.

G.W. Yeates, et al.; "Nematode populations and their effects on herbage production in a volcanic plateau pasture"; New Zealand Journal of Agricultural Research; 1986; vol. 29; pp. 517-523.

G.W. Yeates, et al.; "Effects of oxamyl and carbofuran on nematode populations below 10 grass cultivars"; New Zealand Journal of Experimental Agriculture; 1983; vol. 1; pp. 147-151.

B.G. Zhao, et al.; "Mutualistic symbiosis between Bursaphelenchus xylophilus and bacteria of the genus *Pseudomonas*"; Forest Patholology; 2005; vol. 35; pp. 339-345.

B.G. Zhao, et al.; "Effects of bacteria associated with pine wood nematode (*Bursaphelenchus xylophilus*) on Development and Egg Production of the Nematode"; Journal of Phytopathology; 2007; vol. 155; pp. 26-30.

H. Ferris; "The Nematode-Plant Expert Information System"; NEMAPLEX. Web: http://plpnemweb.ucdavis.edu/nemaplex/Nemaplex.htm http://plpnemweb.ucdavis.edu/nemaplex/plntpara/pltvirus.htm [Access date: Mar. 18, 2014].

\* cited by examiner

NON-NEMATICIDAL COMPOSITION AND USE THEREOF

INTRODUCTION

The invention relates to improvement of growth, yield or marketable-grade of plants grown in media infested with plant-pathogenic nematodes, to levels comparable with those otherwise achieved through nematicidal treatment alone. Plant pathogenic nematodes cause extensive damage to crops, reducing performance, yield and marketable grade, ultimately giving rise to extensive economic loses. Recent estimates contribute $100 billion in losses worldwide due to nematode associated crop losses, half of which are attributed to *Meloidogyne* spp. (Bird and Kaloshian, 2003 and Loison M, 2012). The range of economically important crop species affected by pathogenic nematodes is extensive, encompassing those native to sub-tropical, tropical and warm temperate regions alike. Economically important plants affected by pathogenic nematodes include: grain legumes (e.g. soybean, peanut, bean and peas), vegetable crops, ornamental, nursery and flower crops, cereals (e.g. maize, rice, wheat), root and tuber crops (e.g. potato, sweet potato, yams, cassava, taro, ginger, carrot, sugar beet), plantation, tree and cash crops (e.g. banana, plantain, black pepper, cotton, coconut, citrus crops, coffee, pineapple and sugarcane) and deciduous fruit and nut crops (Bridge and Starr, 2007).

The most effective and widespread means of controlling nematode-associated diseases involves the direct killing of the nematodes themselves and/or reduction of nematode population numbers. These methods vary from chemical control (nematicidal agents), biofumigation and soil solarisation; each of which inflict varying amounts of damage to the ecological environment and/or are restricted in their scope of application. Many chemical nematicides have been shown to have negative effects on human health (e.g. neurotoxicity). In light of such effects, nematicidal treatments are being increasingly restricted in their use (Chitwood D J, 2003 and Gowen S R, 1992). Thus, there is a need to develop methods of controlling plant pathogenic nematodes and other pests in a manner which is not damaging to human health or the environment. However, for safer treatments to be effective and economically viable, they must provide benefits to the agricultural sector in the form of enhanced plant performance and marketable grade, to levels otherwise achieved through the usage of current nematicidal treatments. Moreover, scientific validation of safer alternatives requires robust and independent field trials to demonstrate that such effects are reproducible. Few safe alternatives to the chemical control of plant nematodes have undergone this level of scientific validation, and many natural alternatives to chemical control are either lacking in effectiveness, reproducibility or are not viable economically. The lack of safe and viable alternatives to use of dangerous nematicides is addressed by the present invention.

Human Health Implications of Nematicide Use.

The term 'Nematicidal' refers to the lethal action of a nematicide on specific and essential processes within nematode tissues (Nolin J W, 2002). Nematicides have widespread usage throughout the world in agriculture in reducing plant parasitic nematode numbers and in turn, reducing nematode-related crop losses and maximizing overall yield. There are several classes of nematicides which are categorised in accordance with mode of application or specifics of their mode of action. While mechanisms vary, nematicides must achieve reductions in population size of these parasites where applied. Nematicides may be classed as fumigant nematicides or non-fumigant nematicides. Examples of fumigant nematicides are: 1,3 dichloropene, 2 dimethyl dibromide, methyl bromide, methyl iodide, chloropicrin, and metam sodium and potassium. Following application in liquid form, fumigant nematicides rapidly vaporize and move through open air spaces in soil as a gas, and in doing so, exert their nematicidal effects (Reviewed by Nolin J W, 2002). The mode of action of broad spectrum fumigant nematicides involves the penetration of the agent directly through the nematode body wall. Once inside the body cavity of the nematode, internal organs are affected, resulting in death. Broad spectrum fumigants typically do not require ingestion directly by the nematode (Reviewed by Nolin J W, 2002).

Examples of non-fumigant nematicides are: Vydate® (active ingredient: oxamyl), Temik, Mocap, Nemacur, and Counter. They are formulated as either liquid or granules and when applied, move in soil water by downward percolation where they exert their nematicidal effects. The nonfumigant nematicides are sometimes classified as contact or systemic nematicides on the basis of whether they kill nematodes via contact or via plant uptake initially and subsequently affecting the nematodes feeding on the plant cellular fluids (Reviewed by Nolin J W, 2002). Non-fumigant nematicides such as carbamates (Temik, Vydate®) and organophosphates (Mocap, Nemacur) are highly toxic to insects, disrupting normal behaviour and causing paralysis and death. Non-fumigant nematicides have 'narcotic' type effects which accounts more for nematode mortality rather than direct killing (Reviewed by Nolin J W, 2002). By disrupting nerve impulses and neurotransmission, several aspects of nematode behaviour and development is affected which results in extensive reductions in overall nematode numbers and associated population growth. Overall, toxicity and death associated with systemic nematicides such as Vydate® (oxamyl), Temik and Nemacur, is primarily due to neurological effects which result in disorientation and starvation. At high concentrations over an extended time period, non-fumigant nematicides may be directly lethal against nematodes by inducing more extensive disruption of nerve impulses (Reviewed by Nolin J W, 2002). While effective in counteracting nematode infestation, some nematicides can have toxic effects on humans. Moreover, the risk for toxicity through transmission via human diets is now regarded as significant (EPA, 2010). This has led to increasing regulation and in some cases banning of certain nematicides in the USA and EU in recent years.

The number of persons exposed to pesticides internationally is not known but is likely to be in the tens or hundreds of millions. While some pesticides are selective in the type of pest they kill (EPA 2013), some are not selective and can be toxic to non-target species (Starks S E et al., 2012). In humans, exposure to pesticides can culminate in acute neurological effects and clinical toxicity. In cases where exposures to high levels of pesticides do not result in physician-diagnosed pesticide poisoning, such exposures can contribute to persistent adverse neurological effects (Starks S E et al., 2012). Given the severity of the side effects associated with many pesticides, there are increasing moves worldwide towards reducing or even replacing the usage of several such agents. In particular, EU directive 2009/128/EC requires that member states adopt action plans towards reducing risks associated with pesticide use. Nematicides in particular are undergoing increasing scrutiny by regulatory bodies. Notably, the EU poses have placed tight restrictions on the use of Temik (Aldicarb), a carbamate insecticide and nematicide commonly used in potato production. This is due in-part to the neurotoxic effects attributed to this chemical (Cone M, 2010). Moreover, there is now agreement to terminate all uses of aldicarb in the United States as risk assessments on toxicity data indicate significant toxicity associated with its use (EPA, 2010). In particular, aldicarb has been cited by the EPA as posing potentially "unacceptable dietary risks, especially to infants and young children" (EPA, 2010). However, while aldicarb is being phased out and banned in some countries, there are several other pesticides and nematicides of known toxicity still widely in use today.

It is expected that an increasing number of nematicides and other pesticides will be phased out worldwide in the coming years due to health and environmental hazards associated with their use. Studies have shown that acute neurological effects can occur following exposure to nematicides including organophosphate (OP), and the carbamate classes of nematicides (Farahat T M et al., 2003; Mackenzie Ross S J et al., 2010; Rohlman D S et al., 2011; Roldan-Tapia L et al., 2005). The acute neurological effects and clinical toxicity due to exposure to OPs have been well described. Immediate clinical toxicity may be either mild or acute. Mild effects include dizziness, headache, nausea, vomiting and diarrhoea. Severe acute effects include seizures, cardiac rhythm disturbances, respiratory failure and in some cases coma (Bardin P G, et al., 1994). The effects of acute OP poisoning include chronic neurological sequelae such as reduced neuropsychological performance and increases in other neurological symptoms (Steenland K, et al., 1994; London L, et al., 1998; Rosenstock L, et al., 1991; Stallones L, et al., 2002; Wesseling C, et al., 2002). Chronic neurological effects have also been found on exposure to methyl bromide, a fumigant nematicide (Anger W K., 2003 and O'Malley M A et al., 2011). Replacements for methyl bromide have been put forward, however, these also pose health risk to humans. For example, while oxamyl has been listed as one of several potential alternates to methyl bromide, it is rated as extremely toxic to humans and excess applications can lead to accumulation of residues in foods (UNEP, 2005). To reduce human exposures to oxamyl, Maximal Residue Limits (MRLs) for this chemical in crops have been determined by agencies in a number of countries (FAO/WHO, 2002). However, these reports are sometimes restricted in the scope of crops assessed. At present there is a system for reporting food issues within the European Union via the Rapid Alert System for Food and Feed (RASFF, EU Regulation EC/178/2002). This allows for official controls over point of entry over fruit and vegetables imported from specific countries, with oxamyl and methomyl listed amongst many other hazards (RASFF, EU Regulation EC/178/2002). Recently, the RASFF was cited for providing notification in 2008 of a sample of potatoes in which oxamyl was found to be "at levels which would lead to intakes above the acute reference dose" (ECPRF, 2011). Thus, while restrictions are in place in some jurisdictions, nematicides such as oxamyl have been found to reach unsafe levels in human foods. From a human health perspective therefore, there is a need for safer alternatives to chemical nematicides.

Environmental Implications of Nematicide Use

Pesticides can potentially impact upon non-target species within air, soil and water, including soil bacteria and fungi, pollinators and pest parasites. In 2008, the German Federal Office of Consumer Protection and Food Safety suspended the registration of eight neonicotinoid pesticide seed treatments, one of which was linked to the death of large numbers of honey bees. It is likely that other pesticides and nematicides will face further scrutiny in coming years given that several, including Vydate® (active ingredient: oxamyl), are known to be highly toxic to bees (DuPont™ Vydate® insecticide/nematicide, Technical Bulletin, 2013). There are also concerns over the impact of nematicides on soil environments. This is due to the important roles that biological/microbial communities play in maintaining the health of natural and agricultural soil systems (Ibekwe M, 2004). The impact of nematicides on biological communities on soil is observed to be variable depending on the type of nematicide used, the soil type and the species of biological/microbial communities under study. It is well established that fumigant nematicidal treatments can negatively impact on non-target species such as bacteria and fungi (Ibekwe M, 2004). Moreover, it is well known that fumigant nematicides can drastically impact upon the structure of beneficial free-living nematode communities. For instance, following chloropicrin fumigation on Japanese soybean fields, nematode density was observed to decrease while the dominant taxon switched from Rhabditidae to Cephalobidae (Okada H et al., 2004). In addition, fungal-feeding nematodes were found to be strongly reduced by the fumigant nematicides used on commercial strawberry farms in Southern Spain (Sanchez-Moreno, S., et al., 2010). While some studies indicate such effects to be transient, the long-term repeated use of fumigant nematicides may have more significant and lasting effects on soil microbial populations (Reeve J R et al., 2010).

Unlike fumigant nematicides, those classified as non-fumigant are considered as having little impact on organisms which lack a nervous system (e.g. bacteria, fungi), given that such nematicides generally act by inhibiting cholinesterase in neurons. However, few studies have examined the effect of non-fumigant nematicides on non-target soil animals, such as beneficial species of free living nematodes. Some studies point to non-fumigants such as fosthiazate and imicyafos as having specificity for plant pathogenic nematodes and limited effects on otherwise beneficial free living nematodes (Wada S et al., 2011; Sturz and Kimpinski, 1999; Cowgill et al., 2002; Kimpinski et al., 2005 and Pankhurst et al., 2005). In contrast, the nematicide oxamyl (active ingredient in Vydate®) has been found to decrease total nematode populations and reduce free living nematodes when applied alone or in combination with carbofuran (Yeates et al., 1983, Yeates, 1985; Yeates and Pestridge, 1986 and Smolik, 1977). A recent study also demonstrates a toxic affect of oxamyl against a species of a bacterial feeding nematode *Bursilla* sp., a species with key roles in decomposition and nitrogen cycling (Bell et al., 2006). In particular, a reduction in adult survival and inhibition of egg production was attributed to this nematicide. Adverse effects on bacterial counts were also reported when oxamyl was present at high levels (400 ppm), an effect with further potential environmental impacts (Bell et al., 2006). The authors conclude that non-target impacts on soil nematodes are likely for conventional oxamyl application. Oxamyl and Cyfluthrin have also been found to have non-target effects on reducing numbers of a soil predator which has important roles in pest management (Tillman P G, Mullinix B G Jr et al., 2004). Collectively, these studies highlight the potential negative effects of nematicides on non-target species within the soil, highlighting the need for safer alternatives to conventional nematicides and treatments which do not impact upon soil biological/microbial communities or the environment.

Carbamate pesticides and nematicides are particularly toxic to non-targeted species of wildlife including birds and fish (Grue, C. E., et al., 1983 and Boran M et al., 2007). In spite of their reduced stability in acquatic environments, carbamate nematicides have been found as contaminants in a variety of water sources worldwide including: streams and rivers in Martinique (Bocquené and Franco, 2005), surface waters in Spain (Chiron et al., 1993, 1994), well water in Maine (USA; Bushway R J et al., 1992), and a toxic metabolite of carbaryl (1-naphthol) has been found in surface and groundwater's in the USA and India (Busshway 1981 and Dikshit et al., 1990). In the agricultural zone of the Yaqui Valley located in northwest Mexico, methiocarb and 3-hydroxycarbofuran were also detected in groundwater and surface waters (5.4 micrograms/L and 18 micrograms/L respectively; Garcia de Llasera M. P et al., 2001). Thus, from an environmental and potentially human health point of view, there is much need for safer alternatives to the use of chemical nematicides and pesticides.

On account of human health and environmental concerns, nematicides will face increasing scrutiny and potential bans both in Europe and worldwide in countries such as the United States. Without the development of safer alternatives which can achieve crop yield increases equivalent to those levels otherwise achieved with nematicides, the impact of placing a ban on nematicide usage in food production worldwide, may be significant.

Impact of Climatic Conditions on the Efficacy of Nematicides

Unfavourable environmental conditions are known to adversely influence the efficacy and environmental fate of many pesticides and nematicides, most notably of which is rainfall. While a certain level of rainfall or irrigation water is required for water-soluble non-fumigant nematicides to be transferred and to be effective within the soil region, failures by growers to control nematode infestation whilst using non-fumigant nematicides is a likely consequence of excessive rainfall or irrigation and poor chemical retention within the crops primary rooting zone (Noting et al., 2002). In particular, rain occurring immediately following application of aldicarb may remove the agent from the soil zone, thereby reducing its effectiveness (Sharma et al., 1998). Simulated rainfall of 50.8 mm applied at second and eighth days after aldicarb application, demonstrated a 64% depletion of the nematicide which appeared in effluent in it's oxidised sulfoxide or sulfone form (sandy soil, Bowman B T, 1988). In the case of oxamyl, a UK study indicated that application of the nematicide in the month of June was largely washed from foliage by the occurrence of heavy rain shortly after application (Whitehead et al., 1985). In turn, oxamyl is known to be susceptible to leaching into ground water in areas that have high amounts of rainfall (Dupont Technical Bulletin). Such effects can have a substantial impact on nematicide efficacy over time. For example, inconsistent nematode control when using the nematicide 'ethoprop' and a number of other non-fumigant nematicides was found in Florida over a period spanning two decades (Garcia-M, R and Rich J R, 1983; Nordmeyer D et al., 1982 and Rich J R et al., 1984). Such effects have been attributed to excessive rainfall following nematicide application to deep sandy soils (Garcia-M, R and Rich J R, 1983), and the efficacy and persistence of ethoprop was found to be related to rainfall levels post-treatment of corn (sandy loam soil, Rohde, W. A et al., 1980). Early-season rainfall has also been observed in trials spanning a 12 year period to adversely affect efficacy of non-fumigant nematicides (Rahi G S et al., 1992). Moreover, simulated rainfall experiments demonstrated how 2.5 cm of rain can render ethoprop nematicides ineffective against *M. javanica* species of nematode (Rahi G S et al., 1992).

These studies highlight an inherent limitation of nematicide applications in regions which experience excessive rainfall. Therefore, there is a requirement for treatments which are more robust and less susceptible than nematicides to the unfavourable conditions of high precipitation. This is particularly relevant for regions such as Northern Europe where high levels of rainfall represent a significant problem even during summer months.

Mechanisms of Nematode-Induced Crop Damage

The underlying processes by which nematodes successfully invade plant host tissue, feed and reproduce are highly complex. This in turn poses considerable challenges to the development of technologies or agents which can effectively control or reduce nematode-induced crop damage. The three main classes of pathogenic nametodes are: sedentary endoparasites, migratory endoparasites and migratory ectoparasites.

1. Sedentary Endoparasites:

Root knot and cyst nematodes represent two important examples of sedentary endoparasites. Without effective control measures using agents such as nematicides, root knot nematodes (RKN) attack crops through the root system and inflict a broad range of damage to growing crops worldwide. The primary symptom of infestation is the presence of galls in the roots, the presence of which impacts upon water and nutrient uptake. In particular, nematodes are observed to alter xylem vessels and interrupt water transport (Kirkpatrick, T L, et al., 1991), while several studies point to the disruption of nutrient uptake and translocation (Carneiro, R G, et al., 2002 and references therein). The net effects of infection are reduced crop performance and marketable yield. Significant losses are also observed in sports turf on a global scale, in particular links golf courses. Cyst nematodes such as *Globodera pallida* also cause severe yield losses all over the world, especially in areas of low organic matter soils and particularly affect potato crops.

Mechanisms underlying nematode-induced crops damage are highly complex, both at the level of the parasite itself and that of plant biology. Nematodes are highly successful and effective as parasites and can infect over 2000 plant species, having evolved highly specialized systems for infecting and deriving nourishment from host plant tissue. This can involve the modification of root cells into feeding sites known as syncytia, thus allowing for successful feeding during key developmental and reproductive stages (Hussey et al., 1989). This process requires the secretion of a complex array of effector proteins, the roles of which are still being elucidated (*Hamamouch* N et al., 2012). Root knot nematodes (RKN) of the family *Meloidogyne* are infective at their second stage juvenile phase (J2) during which time they are attracted to and migrate towards the growing plant root, penetrate through the root cap and into the region in which the vascular cylinder undergoes differentiation. Juveniles inject oesophageal gland secretions through the stylet into several undifferentiated procambiel root cells which are transformed into 'giant cells' (reviewed by Hussey, 1989 and Hussey R S and Janssen G J W, 2002). These are feeding sites for the parasite during several stages of the life-cycle and are also a prime source of nematode-mediated damage in the root zone. Once initiated, the nematode enters a sedentary stage of life and undergoes three molts in the process of entering into the adult phase. The females primarily occupy the giant cells. They have a bulbous, saccate shape, are non-motile and produce eggs within three-six weeks of infection. The female continues to grow irrespective of fertilization by males. Following the death of the female, the body encysts to protect the 100s of embryonated eggs which have been produced. This ensures the viability of the eggs in the soils for years. Males on the other hand, gain motility after the third molt, and leave the root in a fusiform shape to enter a free-living stage in the soil (reviewed by Williamson V M, and Hussey R S, 1996). Cyst nematodes (e.g. genera *Heterodera* and *Globodera*) have a similar life-cycle to RKN, including second stage juveniles, the locating and invasion of the root, development of a feeding site for all juvenile stages and adult females, and development of vermiform males (Cook R and Noel G R, 2002). Mating is necessary in some but not all species. Different species can also vary in several biological characteristics which reflect their adaptation to specific ecosystems. Differences include mode of reproduction (sexual or asexual), generation time and number per growing season, hatching (biotic or abiotic simuli), and tolerance to abiotic stresses (Cook R and Noel G R (2002)). While life-cycles are often short, sedentary endoparasites are highly effective in establishing themselves within host plants to the point at which they are highly parasitic, thereby negatively impacting upon plant growth, yield, performance and marketable grade. Examples of sedentary endoparasites include: root knot, cyst and citrus nematodes.

2. Migratory Endoparasites:

Migratory endoparasites are mobile with feeding involving the burrowing into the root and feeding on the internal root cells. These nematodes migrate to and from feeding locations and can give rise to an extensive level of damage to plants within a crop growth area. They may be free living, allowing them to live freely within the soil and feed on plants without requiring attachment. Migratory endoparasites are infective at most life stages. While migratory endoparasites can lay eggs in the soil, most are laid and hatch inside roots. Development within the egg involves development from first stage (J1) to second stage (J2) juvenile. Following J2 hatch, the nematode develops into either male or female following a number of moults. In many species of migratory endoparasites, males are not required for egg fertilization. Examples of migratory endoparasites are: lesion, stem, bulb, burrowing, leaf, stunt, lance and spiral.

3. Migratory Ectoparasites:

These species typically feed on cells within the external epidermis of roots. The life cycle involves the laying and hatch of eggs within the soil, with nematodes emerging as a second stage juveniles (J2) after a number of moults within the egg. Successful feeding by J2 involves migration through the soil, location of a root and feeding on the epidermal cells on the root surface through use of a stylet. The nematode may withdraw the stylet and proceed to feeding at a new location. Development into a $3^{rd}$ stage juvenile is followed by a $4^{th}$ moult, at which stage the nematode is an adult. Examples of classes of migratory ectoparasites are: pin, ring, mint, dagger, sting and stubby-root nematodes.

Nematode Behaviour and Survival

Nematode population survival and success is directly associated with the strategies and mechanisms used to obtain food, reproduce, hatch and move between locations. Sensory receptor systems are critical in this regard, with much of nematode behaviour involving chemoreception, thermoreception and other sensory systems. Migration, kinesis and taxis represent important aspects of nematode behaviour, with movements of many nematode species directed by means of chemotaxis, thermotaxis, gravitaxis other mechanisms. Thermoreception and thermotaxis are particularly important to nematodes in terms of influencing their dispersion and search for food sources, while sex hormones or pheromones frequently play crucial roles in reproduction.

In addition to requiring success in obtaining food sources, obtaining sufficient levels of nutrition and successfully reproducing, both pathogenic and beneficial nematode populations alike must also respond to and survive pressures induced by abiotic and biotic stresses. Nematodes like other Animalia respond to infections such as bacteria and fungal pathogens by inducing expression of host defence genes. Many of the genes present within nematode genomes are homologous to or have evolutionary relationships to those found in higher animals. For example, the *Caenorhabditis elegans* genome contains the scavenger receptor (SRs) family of proteins which are orthologues of those in higher animals. Nematodes also have genes with evolutionary relationships to C-type lectin-like receptors of the DECTIN-1 cluster in higher animals, albeit not othologous to any specific receptor (Means T K 2010 and Sattler S et al., 2012). Additional, nematodes have acquired a number of genes from bacteria and fungi. One notable acquisition to the nematode genome is the endo-beta-1,3-glucanase gene which appears to have been acquired by several species of pathogenic nematodes, most likely through horizontal gene transfer mechanisms with bacteria (Kikuchi et al, 2005). Hence, the success of nematodes within their ecosystems and niches is a function of their long evolutionary history, involving maintenance of important functional gene families and acquisition of other genes from sources such as bacteria and fungi. It is this long evolutionary history which has allowed nemtodes to evolve to a position where they occupy a huge variety of ecological niches. Likewise, many other components of the ecosystem have also evolved to live and succeed within the nematode ecosystem. This has givin rise to a multitude of other pathogens which use nematodes as vectors for successfully infecting plants.

Nematodes as Viral Vectors and their Interactions with Other Pathogens:

Plant pathogenic nematodes are host to a wide range of pathogens which infect plants. Examples include viruses such as Tobraviruses and Nepoviruses (Ferris H, 2001 and references therein). Examples of Tobraviruses include: Tobacco rattle virus (TRV), Pea early-browning virus (PEBV) and Pepper ringspot virus (PepRSV) and tomato black ring virus. TRV, for example, is plant pathogenic virus which causes spraing in potatoes, the effects of which reduces crop quality. Vectors of TBV include stubby root nematodes of the family Trichodoridae. Plants typically become infected with the virus when nematodes begin feeding.

Nepoviruses are largely transmitted to plants by dagger and needle nematodes of the *Xiphinema* and *Longidorus* genera (Ferris H, 2001 and references therein). *X. americanum* transmits tobacco and tomato ringspot viruses. Strains include: peach rosette mosaic virus, peach yellow bud mosaic virus, cherry rasp leaf virus, grapevine yellow vein virus. *X. californicum*, *X. rivesi* and *X. brevicolle* have been reported as viral vectors also. Prune brown line and *Prunus* stem pitting strains of tomato ringspot virus and the cherry leaf mottle strain, can be transmitted to crops by *X. californicum*. *Arabis* mosaic virus is transmitted to crops by *X. diversicaudatum*, while grapevine fanleaf virus is transmitted by *X. index*. Longidorus *elongatus* transmits tomato blackring and raspberry ringspot viruses (Ferris H, 2001 and references therein). Plant pathogenic nematodes therefore, are observed to act as vectors for a range of other pathogens which negatively affect crop yield and/or quality. Since the lifespan of certain nematodes species can extend for several years, populations can remain infective during this time and continually re-infect crops with viral pathogen over several seasons.

Plant pathogenic nematodes are observed to 'interact' with and/or exacerbate a number of plant diseases. An example of this is the involvement of lesion nematodes in Potatoe Early Dying Disease. Co-infection of potato with *Pratylenchus penetrans*, increases the severity of potato early dying disease, directly caused by *Verticillium* dahlia (LaMondia 2006 and references therein). Thus, there is a significant impact of nematodes on the severity of co-infections and other diseases.

Alternative Methods of Reducing Nematode-Induced Crop Damage

Methods of preventing nematode-induced damage predominantly focus on nematicidal approaches, i.e. killing the parasite directly or disrupting neurotransmission to cause disorientation and starvation and ultimately death to the parasite and reduction of population size. Since the 1970s, there has been considerable interest expressed in the potential to develop natural approaches to pest management, which do not repy exclusively on chemical or other nematicidal treatments. However, most natural approaches developed in this time are less effective than mainstream nematicides and do not provide the same positive effects on enhancing growth and yield in the face of nematode challenge.

A method of nematode control was proposed by Triantaphyllou, A. C. (1973) which suggests the targeting of population dynamics of nematodes given that crop damage is most often proportional to the female population, particular in the case of some species of sedentary endoparasites. Mechanisms which determine the sex of nematodes include Genetic Sex Determination (GSD) and Environmental Sex Determination (ESD). GSD requires fertilization by males but in the absence of males, meiotic and mitotic parthenogenetic (i.e. asexual reproduction without fertilization) pathways take place in many species of root knot nematodes (RKN) to give rise to production of viable eggs (see Castagnone-Sereno, P. 2006 and references therein). Sex determination in RKN and other species such as cyst nematodes (e.g. genera *Heterodera* and *Globodera*), is highly influenced by external environmental factors including quality of host tissue and population size. Under favourable, non-stressed conditions, development of J2 juveniles into females is favoured, while stressed conditions are associated with increased proportions of males developing from J2. Such shifts in ratio may be due to an ESD mechanism influencing sexual development (Ellenby, C. 1954, Grundler, F et al., 1991, Trudgill, D. L., et al., 1967), From an agricultural perspective, it would be advantageous to develop a viable means of shifting the sex ratio of certain nematode populations towards the male direction (Triantaphyllou, A. C., 1973) and thus, in the direction of decreased pathogenicity and increased plant performance.

Other alternative methods of pest control have been proposed, such as 'microorganismal manipulation' of the host sexuality. Dagger nematodes, for example, are host to symbiotic, cytoplasmic bacteria which are transmitted exclusively via the maternal line, for example, *Verrucomicrobia* species (Vandekerckhove et al., 2000 and references therein). Males are rare in these populations, with females reproducing asexually and with a tendency to produce females. It has been suggested that microbes which are inherited maternally in this manner may have an evolutionary advantage if they can drive the host sex ratio in a direction favourable to the growth of their population, i.e. towards the female direction (Vandekerckhove et al., 2000 and references therein). In terms of nematode control, any mechanism which could alter the nematode ratio towards males may provide a means of reducing crop damage, given that there would be a lower incidence of females reproducing asexually at the population-wide level. Of note, bacteria-like endosymbionts and other associated bacteria have been described for several other classes of nematodes, including cyst nematodes (*Heterodera*), burrowing nematodes (Radophoblus) and pinewood nematodes, (*Bursaphelenchus xylophilus* and *B. mucronatus*). Several bacteria species associated with pinewood nematodes, including certain strains of *Pseudomonas*, have been found to be associated with significant increase in nematode reproductive rates, while others have been shown to have suppressive effects (Zhao and Lin, 2005 and Zhao et al., 2007). It has also been suggested that bacterial symbionts may improve nematode growth and/or reproduction through reciprocal exchange of nutrients or producing factors which contribute to pathogenicity. The relationship between nematodes and the microbiome may also provide complementary pathways in detoxification metabolism (Cheng 2013 and references therein). While a theoretical potential for controlling of nematodes through mechanisms involving reproduction, metabolism, digestion and/or factors related to pathogenesis exists, technologies which can achieve these effects in a manner safe to both the environment and human health have not been developed to date.

Natural approaches to controlling nematode-induced crop damage have been relatively unsuccessful. Almost 30 years have passed since such approaches were investigated by the scientific community with few natural alternatives developed to rival commercial nematicidal treatments since. However, such approaches remain attractive given the increasing understanding of the health and environmental implications of mainstream nematicides by the scientific and medical community alike and the increasing governmental control placed on these agents worldwide in recent years, a trend which is likely to continue in decades to come. Moreover, there is a growing body of scientific evidence which suggests that rather than killing plant pathogenic nematodes, there are significant benefits to be gained from maintaining and managing their presence within the soil ecosystem. In particular, harmful species of nematodes are increasingly viewed as being integral and potentially useful components of soil systems (reviewed by Neher Da, 2010). While negative effects of plant pathogenic nematodes are well described, their positive role in ecosystems and agriculture are beginning to be appreciated. For example, *Heterodera trifolii* Goffar, a species of pathogenic cyst nematode which feed on roots of clover (*Heterodera trifolii*), has been shown to be associated with increased root growth, microbial biomass and transfer of 15N to neighbouring plants, in grasslands containing white clover and *Lolium perenne* (Perennial Ryegrass; Bardgett et al., 1999). Moreover, increases in root growth in host clover plant (+141%) and the uninfected neighbouring ryegrass (+219%) were achieved in the presence of this species of pathogenic nematode. This suggests an important role for plant pathogenic nematodes within the broader ecosystem by contributing to carbon and nitrogen transfer below-ground and giving rise to enhancement in root growth in unaffected neighbouring plant species. Similar growth regulatory effects within the broader plant community have been observed for short-grass prairie (Ingham R E 1985) in addition to a positive correlation between root-feeding nematodes and increased root biomass in mid-successional grasslands (de Deyn G B et al., 2004). Moreover, the presence or absence of root-feeding nematodes has been found to dramatically affect the type(s) and growth rate of plant species (de Deyn G B et al., 2004). These studies emphasis the important role that plant pathogenic nematodes play within the soil and how their biotic interactions and their feedback within the ecosystem can impact upon the plant growth within the community. On the basis of such studies, there is a growing move currently taking place amongst the scientific and agricultural community alike. In particular, the use of organic amendments to enhance disease suppression in crops is likely to be enhanced in the future by applying ecological concepts related to nematode strategies of coexistence of different nematode species which share the same resource (Neher D A et al., 2010). Natural approaches to counteracting the negative effects of pathogenic nematodes therefore, need not require treatments to act in a nematicidal manner.

New treatments to counteracting nematode infestation have been developed in recent years, each with their own advantages and limitations. Limitations include difficulties in producing the agents, limited duration of efficacy, dependence of efficacy on nematode species and little effects on nematode multiplication (Loison M et al., 2012). For a natural alternative to chemical nematicides to be viable they must provide increases in yield and marketable grade on-par with those achieved using commercially available nematicidal treatments, with effects consistent against a range of nematode species, with the product economically viable and its effectiveness verifiable on a large commercial scale.

STATEMENTS OF INVENTION

According to the invention there is provided the use of a non-nematicidal composition comprising at least one glucan and/or at least one fucan which act individually or synergistically with mannitol to reduce losses in crop yield and marketable grade caused by the infestation of growth media with plant pathogenic nematodes, to levels equivalent to those achieved with commercial nematicides, but without posing a risk to the ecosystem or user.

The invention encompasses the use of glucan alone, fucan alone, glucan with mannitol, fucan with mannitol, glucan with fucan, and glucan with fucan and mannitol.

The composition may comprise at least one glucan.
The composition may comprise at least one fucan.
The composition may comprise at least one glucan and at least one fucan.
The composition may comprise at least one glucan and at least one mannitol.
The composition may comprise at least one fucan and at least one mannitol.

The invention also provides the use of a non-nematicidal composition comprising at least one glucan and/or at least one fucan or at least one mannitol in combination with glucan and/or fucan for decreasing losses in crop yield and marketable grade due to the infestation of growth media with plant pathogenic nematodes, without posing a risk to the ecosystem or user. The composition may comprise a weight/weight ratio of between approximately 1:1:1 to 1:1:3 of at least one glucan:at least one fucan:at least one mannitol. The composition may comprise a weight/weight ratio of about 1:2:3 of at least one glucan:at least one fucan:at least one mannitol. In one case the ratio is 1:1:1. In another case the ratio is 1:1:2. In another case the ratio is 1:1:3.

Advantageously, the compositions described herein:
have no impact on the environment;
leave no residues;
are not harmful to person applying the composition;
are not harmful to consumers of crops;
maintain the balance of soil ecosystem
are not harmful to bees; and
provide an environmentally and economically safe alternative to nematicides (equally efficacious to commercially available nematicides)

The at least one glucan may be a beta glucan, the beta glucan may be (1→3) or (1→6) glucan. The at least one glucan may be laminarin.

The at least one fucan may be an alpha-fucan, the at least one fucan may be fucoidan.

The at least one glucan and/or the at least one fucan and/or the at least one mannitol may be isolated from a brown macroalga of the class Phaeophyceae. The brown macroalga of the class Phaeophyceae may be derived from one or more of the families Laminariaceae, Fucaceae or Lessoniaceae.

The at least one glucan and/or the at least one fucan and/or the at least one mannitol may be isolated from a brown macroalga of the *Ascophyllum* species.

The at least one glucan and/or the at least one fucan and/or the at least one mannitol may be isolated from a brown macroalga of the *Laminaria* species.

The at least one glucan and/or the at least one fucan and/or the at least one mannitol may be isolated from a brown macroalga of the *Sargassum* species.

The at least one glucan and/or the at least one fucan and/or the at least one mannitol may be derived from red alga, the red alga may be Florideophyceae.

The least one glucan and/or at least one fucan or at least one mannitol in combination with glucan and/or fucan may be produced by means of synthetic chemistry and/or biotechnology-related approaches.

The at least one glucan may be derived from species of fungi, the fungi may be a yeast such as *Saccharomyces cerevisiae*.

In one aspect the invention provides the use of mannitol for treating crops in nematode infested soils.

The pathogenic nematodes may be selected from one or more of the group comprising: migratory ectoparasites, sedentary endoparasites or migratory endoparasites.

The pathogenic nematodes may be selected from one or more of the group comprising: root knot, cyst, stem, bulb, citrus, reniform, lesion, pin, stubby-root, sting, stunt, burrowing, lance, dagger, anguina, spiral, ring, sheath, sheathoid, seed gall, spring dwarf, summer dwarf, spine, sessile, awl, pine wood, needle, mint, foliar, leaf, false root knot or rice root nematodes. The pathogenic nematodes may belong to one or more of the families: Heteroderidae, Anguinidae, Pratylenchidae, Tylenchulidae, Hoplolaimidae, Trichodoridae, Belonolaimidae, Longidoridae, Criconematidae, Aphelenchoididae, Dolichodoridae or Parasitaphelenchidae. The pathogenic nematodes may belong to one or more of the genus: *Heterodera, Globodera, Meloidogyne, Ditylenchus, Pratylenchus, Tylenchulus, Rotylenchulus, Gracilacus, Trichodorus, Paratrichodorus, Belonolaimus, Merlinius, Quinisulcius, Tylenchorhynchus, Radopholus, Hoplolaimus, Xiphinema, Anguina, Helicotylenchus, Scutellonema, Mesocriconema, Hemicycliophoras, Hemicriconemoides, Aphelenchoides, Cacopaurus, Dolichodorus, Bursaphelenchus, Hirschmanniella, Longidorus, Aphelenchoides* or *Nacobbus*.

The invention also provides a method of reducing losses in crop yield and marketable grade caused by the infestation of crop growth media with plant pathogenic nematodes without posing a risk to the ecosystem or user comprising the step of:

applying a composition comprising at least one glucan and/or at least one fucan or at least one mannitol in combination with glucan and/or fucan, to the crop growth media and/or a plant being grown in the crop growth media wherein the composition is applied in an amount such that about at least 60 grams/Hectare of at least one glucan and/or at least one fucan or at least one mannitol in combination with glucan and/or fucan is applied to a crop growing area.

The invention encompasses the use of glucan alone, fucan alone, glucan with mannitol, fucan with mannitol, glucan with fucan, and glucan with fucan and mannitol.

The composition may comprise at least one glucan.

The composition may comprise at least one fucan.

The composition may comprise at least one glucan and at least one fucan.

The composition may comprise at least one glucan and at least one mannitol.

The composition may comprise at least one fucan and at least one mannitol.

The composition may be applied in an amount greater than 60 grams/Hectare of at least one glucan and/or at least one fucan or at least one mannitol in combination with glucan and/or fucan, in order to provide increased yield and marketable grade subject to return on investment from the application, wherein the amount is increased approximately 10-fold. By "marketable grade" is meant the grade of production as defined by size and quality parameters of the crop, vegetable, fruit, seeds or plant biomass, which is capable of being sold and meets required quality standards.

The invention further provides a method of reducing losses in crop yield and marketable grade caused by the infestation of crop growth media with plant pathogenic nematodes without posing a risk to the ecosystem or user comprising the step of:

applying a composition comprising at least one glucan, at least one fucan, and at least one mannitol to the crop growth media and/or a plant being grown in the crop growth media wherein the composition is applied in an amount such that about at least 60 grams/Hectare of at least one glucan and at least one fucan and at least one mannitol is applied to a crop growing area.

In one case the ratio is 1:1:1. In another case the ratio is 1:1:2. In another case the ratio is 1:1:3.

The composition may be applied in amount such that greater than 60 grams/Hectare of at least one glucan and/or at least one fucan or at least one mannitol in combination with glucan and/or fucan is applied to the growing area in order to promote increased yield and marketable grade subject to return on investment from the application, wherein the amount is increased approximately 10 fold.

Advantageously, the compositions described herein may prevent losses in crop yield and marketable grade caused by the infestation of growth media with plant pathogenic nematodes to levels equivalent to those achieved with commercial nematicides but without posing a risk to the ecosystem or user. By 'ecosystem' is meant a biological community of interacting organisms and their physical environment. The ecosystem may be terrestrial and/or aquatic. Terrestrial ecosystems are ecosystems which occur on land and include tundra, taiga, temperate deciduous forest, tropical rain forest, grassland and desert. Aquatic ecosystems are those which occur in bodies of water including freshwater and marine ecosystems. Basic constituents of ecosystems include biotic components, for example, producers (autotrophs), consumers and decomposers. Biotic components comprise the soil food web within ecosystems and may include bacteria, algae, fungi, oomycetes, virus, viroids, virus-like organisms, lichens, protozoa, nematodes, arthropods, insects, aphids, mites, vertebrates, invertebrates and plants. In addition to biological components, physical and chemical components and compounds form key parts of ecosystems and include organic matter, inorganic matter, micronutrients, macronutrients, minerals and gases. Other constituents of ecosystems include abiotic components, for example, water, rain, humidity, light, radiation, temperature, climate, atmosphere, air, latitude, altitude and factors affecting pH. The growing area, growth substrate or media in which organisms within an ecosystem grow may be solid, liquid or semi-solid and may be biotic and/or abiotic. The types of species within ecosystems include native species, immigrant species, indicator species and keystone species. Species within an ecosystem interact in a number of ways, including by means of interspecific competition, predation, parasitism, mutualism or commensalism Important cycles which occur within ecosystems include the Biogeochemical Cycle, Carbon Cycle, Nitrogen Cycle, Phosphorus Cycle, Sulfur Cycle and the Hydrologic Cycle (water cycle).

The compositions described herein do not pose any risk to terrestrial ecosystems and they are not nematicidal. Furthermore, the compositions do not negatively impact on general biota within the growing area. Moreover, the compositions do not negatively impact on water quality as can otherwise occur with other nematicide treatments, nor do they lead to dangerous chemical run-off into the wider environment and aquatic ecosystems, as can otherwise occur with some nematicides. The compositions do not pose any hazard to bees as can occur with some nematicides. Additionally the compositions do not negatively impact on abiotic components or physical or chemical components of the ecosystem. The compositions described herein do not pose any risk to the user and are widely used as dietary supplements in animals and humans. Two individual constituents of the compositions, glucan and/or fucan, have been isolated and are used as dietary feed additives to enhance animal health, either individually or in combination (McDonnell et al., 2010). The third constituent, mannitol, is widely used in foods and as an artificial sweetener.

The composition may be applied to a member of the Kingdom Plantae or growth area containing a member or members of the Kingdom Plantae, optionally at root developmental stages, such as one or more of: root primordium formation, root meristem formation, establishment of tissue systems, root elongation or root hair formation.

The composition may be applied to the plant during tuber growth and developmental stages, such as one or more of: sprout development, vegetative growth, tuber initiation, tuber growth or tuber maturation. First application of the composition may be at 50% post-emergence followed by application at regular weekly intervals for a period of four to six weeks.

The composition may be applied at regular intervals during key plant developmental stages.

The composition may be applied at a point in time in which root and/or shoot emergence is deemed optimal.

The composition may be applied at a preferred application rate of at least 60 g/Ha of bioactives, optionally at least 64 g/Ha, at least 70 g/Ha, at least 80 g/Ha, at least 90 g/Ha, at least 100 g/Ha, further optionally at levels between 100 and 400 g/Ha, further optionally at levels ≥400 g/ha of bioactives.

The composition may be applied as a pre-sowing treatment, either to the seed prior to germination or to the seed post-germination and/or prior to it being sown.

The composition may be applied in accordance with the diversified germination behaviour of the seed population, with first fertirrigation or soil application taking place one week after sowing and at regular intervals subsequently thereafter, also by fertirrigation or soil, with the total duration and timing of intervals dependent on the life-cycle characteristics of the particular nematode species targeted and the root growth, vegetative growth and/or reproductive growth of the crop in use.

The composition may be applied in accordance with the diversified germination behaviour of the seed population, with first foliar application taking place at 50% post-emergence, followed by applications who's total duration and timing depend on the life-cycle characteristics of the particular nematode species targeted and the root growth, vegetative growth and/or reproductive growth of the crop in use.

The composition may be applied to annual plants and/or their growth media at various time points including seed sowing, between seed sowing to harvest, post harvest and/or pre-sowing, optionally within one growing season.

The composition may be applied to biennial plants and/or their growth media at time points throughout the two year life cycle.

The composition may be applied to perennials and/or their growth media at planting, growing, blooming, seeding and post-harvest periods throughout a number of years.

The composition may be applied at points in time either prior to the growing season, during the growing season, at the end of the growing season, just after the growing season, or outside of the growing season, such as during summer or winter off-season periods or periods of crop rotation.

The composition may be applied to the plant and/or growth media of cool season crops, cover crops or turf grass.

The composition may be applied during processes of winter seeding, spring seeding, summer seeding, frost seeding, dormancy seeding or overseeding.

The composition may be applied as a single application.

The composition may be applied as a treatment for the purposes of enhancing or maintaining quality, viability, shelf-life and/or to prevent storage or transport-related losses.

The composition may be applied in the presence of a fertilizer other active ingredients or bionematicides, such as fungicides, pesticides, herbicides, insecticides, biostimulants, plant strengtheners, nematicides, nematophagous fungi or bacteria, rhizobacteria, endophytic fungi, chemoattractants, hatch stimulating agents, nematodes, beneficial nematodes or species of fungi or bacteria, optionally selected from one or more of the group comprising: *Trichoderma* spp., *Bascillus* or *Pseudomonas* spp, and *Pseudomonas fluorescens*.

The plants may be selected from families of non-flowering, seed producing plants belonging to the Gymnospermae division.

The plant may be selected from families within the Bryophyta and Pteridophyta divisions.

The plants may be selected from families of flowering plants belonging to the Angiospermae division, including Solanaceae, Poaceae, Brassicacea and Amaranthaceae. The plant belonging to the Solanaceae family of flowering plants may be selected from potato (*Solanum tuberosum*), tomato (*Solanum lycopersicon*), pepper (*Capsicum* spp), eggplant (*Solanum melongena*), petunia (*Petunia hybrid*), tree tomato (*Cyphomandra betacea*), pepino (*Solanum muricatum*), naranjilla (*Solanum quitoense*) and coffee (*Coffea Arabica*). The plant belonging to the Poaceae family of monocotyledonous flowering plants may include species of maize, wheat, millets, rice, bamboo, common bentgrass, creeping bentgrass, velvet bentgrass, ryegrass or species used in sports turf. The plant belonging to the Brassicaceae family of flowering plants including species of *Brassica oleracea, Armoracia rusticana, Brassica rapa, Brassica napus, Matthiola*, and *Raphanus sativus*.The plant belonging to the family Amaranthaceae family of flowering plants may include species of beetroot and spinach.

Enhanced growth may be conferred in vegetative or reproductive plant organs, optionally selected from root, rhizoid, stem, leaves, flower, seed, fruit, cones, strobili or spores.

The growth media may be infested with plant pathogenic nematodes, optionally root knot, cyst, stem, bulb, citrus, reniform, lesion, pin, stubby-root, sting, stunt, burrowing, lance, dagger, anguina, spiral, ring, sheath, sheathoid, seed gall, spring dwarf, summer dwarf, spine, sessile, awl, pine wood, needle, mint, foliar, leaf, false root knot or rice root nematodes, optionally belonging to the family Heteroderidae, Anguinidae, Pratylenchidae, Tylenchulidae, Hoplolaimidae, Trichodoridae, Belonolaimidae, Longidoridae, Criconematidae, Aphelenchoididae, Dolichodoridae or Parasitaphelenchidae, optionally belonging to the genus *Heterodera, Globodera, Meloidogyne, Ditylenchus, Pratylenchus, Tylenchulus, Rotylenchulus, Gracilacus, Trichodorus, Paratrichodorus, Belonolaimus, Merlinius, Quinisulcius, Tylenchorhynchus, Radopholus, Hoplolaimus, Xiphinema, Anguina, Helicotylenchus, Scutellonema, Mesocriconema, Hemicycliophoras, Hemicriconemoides, Aphelenchoides, Cacopaurus, Dolichodorus, Bursaphelenchus, Hirschmanniella, Longidorus, Aphelenchoides* or *Nacobbus*.

Increments in growth, yield or marketable-grade of plants may be achieved by enhancing tolerance to biotic stress and/or secondary diseases, altering food supply or favourably interfering with the nematode life-cycle, fecundity, development or digestive system in the direction of decreased pathogenicity.

Increments in growth, yield or marketable-grade of plants may be achieved by either positively or negatively altering nematode behaviour and/or behavioural responses in the direction of decreased pathogenicity, optionally by affecting sensory receptors, chemoreception, thermoreception, kinesis and/or taxis, further optionally by affecting chemotaxis, thermotaxis and/or gravitaxis, further optionally by affecting systems or factors which influence hatch.

Increments in growth, yield or marketable-grade of plants may be achieved without posing a risk to the ecosystem or user.

The population dynamics and/or population density of free living nematodes may be maintained and/or altered to levels which enhance the overall soil, soil ecosystem, soil fertility, levels of soil biota and microbiota and/or to levels which reduce numbers of other pathogens and/or pests. The free living nematodes may be selected from parasitic and/or beneficial bacteria/fungal feeders, further optionally species classified as colonizers and or persisters.

The microbiota may be selected from species of bacteria or fungi resident within soil and/or plant ecosystems and may include: species resident within the nematode intestinal tract, soil-derived gut bacteria, species which form part of nematode-bacterium symbioses, species present in eggs and/or cysts, species which form part of entomopathogenic nematode-bacterium complexes, species which influence nematode reproduction, nematophagous bacteria, rhizobacteria, endophytic fungi and/or soil bacteria or fungi which provide micro- and/or macro-nutrients in bioavailable forms.

The total number of nematodes within the population infesting the crop growth media may not be significantly reduced.

Crop yield and marketable grade may be enhanced in conditions known to otherwise negatively impact on the efficacy of commercial nematicides, optionally non-favourable weather or climatic conditions, further optionally, high rainfall.

Crop yield and marketable grade may be enhanced to levels comparable with nematicides, without posing any health risk or hazard to the individual applying the composition.

Crop yield and marketable grade may be increased to levels comparable with nematicides without posing a danger to bees or harming bee populations.

The compositions described herein may enhance growth, yield or marketable-grade of plants grown in media infested with plant-pathogenic nematodes, to levels comparable with DuPont™ Vydate® (oxamyl) and other registered nematicidal treatments, without requiring a reduction in nematode numbers.

The compositions described herein may provide a means of increasing growth, yield or marketable-grade of plants, in the presence of other active ingredients such as fungicides, pesticides, herbicides, insecticides, biostimulants, plant strengtheners, nematicides, bionematicides, nematophagous fungi or bacteria, rhizobacteria, endophytic fungi, chemoattractants, hatch stimulating agents, nematodes, beneficial nematodes or species of fungi or bacteria, optionally selected from one or more of the group comprising: *Trichoderma* spp., *Bascillus* or *Pseudomonas* spp, and *Pseudomonas fluorescens*.

The inventors have found that a particular composition, consisting of a high proportion of β-glucans and α fucans and mannitol is able to act to enhance growth, yield and marketable grade of crops grown in soils which are infested with species of parasitic nematodes, to levels comparable to and statistically indistinguishable from DuPont™ Vydate® (oxamyl) and other registered nematicidal treatments. Moreover, the composition provides these benefits without posing a risk to the ecosystem, without posing any health risk or hazard to the individual applying the composition, nor posing a danger to bees or harming bee populations.

We describe a composition comprising at least one glucan, at least one fucan, mannitol and at least one glucan and at least one fucan, or at least one glucan and mannitol, or at least one fucan and mannitol for use for use in increasing growth, yield or marketable-grade of plants grown in media infested with plant-pathogenic nematodes, to levels comparable with DuPont™ Vydate® (oxamyl) and other registered nematicidal treatments, the use comprising application to the plant and/or growth media.

The composition may comprise at least one glucan. When the composition comprises more than one glucan, each glucan may be the same glucan or a different glucan. Optionally or additionally, the composition may comprise at least one fucan. When the composition comprises more than one fucan, each fucan may be the same fucan or a different fucan. Optionally or additionally, the composition may comprise mannitol. Optionally, the composition may comprise at least one glucan, at least one fucan, mannitol or a mixture or combination thereof.

Optionally, the composition may be applied to the plant at key developmental or growth stages including root development stages, tuber growth and development stages, stages of vegetative growth, bulking, maturation and/or reproductive development. By "root development" stages is meant during the periods of time in which the following take place: root primordium formation, root meristem formation, establishment of tissue systems, root elongation and root hair formation. By "tuber growth and development stages" is meant during the periods of time in which the following take place: sprout development, vegetative growth, tuber initiation, tuber growth or tuber maturation. By stages of "vegetative growth" is meant during the periods of time during which vegetative growth occurs. By "bulking" means the time period in which tuber cells undergo expansion, increasing in size and weight. By "maturation" is meant the period of time in which dry matter of the plant, tuber or fruit reaches a maximum level. By "reproductive development" is meant the period of time encompassing flower development or fruiting.

Optionally, the composition may be applied to the growing area either before, during or after planting. By "growing area" is meant the area containing or supporting the growth of a particular plant, optionally including the underlying growth material, growth media and/or the plant itself. Optionally, the composition may be applied to the plant as a pre-sowing treatment. By "pre-sowing" is meant during the period of time before the seed has been planted into the field or growth media. By "seed treatment" is meant that the seeds have been treated with the composition diluted in a specific concentration in water and/or other compositions or liquids. Optionally, the "seed treatment" refers to the process of "biopriming", a process which confers seed hydration and inoculation of the seed with bioactive compounds or beneficial organisms(s). Further optionally, the seed treatment may refer to a process in which the composition invokes "priming-induced stress tolerance". By "priming-induced stress tolerance", means the period of time or duration of seed treatment necessary to confer 'priming memory' in seeds. By 'priming memory' is meant a process which can help the plant to attain greater stress tolerance to subsequent stress-exposures to the germinating seeds or growing plant. By "stress exposure" is meant the negative impacts on living organisms which occur due to exposures to factors which are either "biotic", "abiotic", or both. By "abiotic" stress is meant a negative impact(s) of non-living and abiological factors on a processes within living organism(s) within a specify environment. Optionally, this may include heat, drought, frost, salinity, flooding, poor drainage, physical breakage, nutrient deficiencies, excess of soluble minerals, wind or fire. Further optionally this may include stresses which are man-made, optionally including compaction of soil, pollution, irrigation, herbicide application or poor horticultural techniques. By 'biotic" stress is meant a stress or negative impact(s) on processes which occurs in a living organism as a result of damage induced by the presence of other living organisms or biological factors on a processes within living organism(s) within a specify environment, which may be caused by bacteria, fungi, oomycetes, viruses, viroids, virus-like organisms, parasites, nematodes, protozoa, insects, aphids, mites, weeds, or other plants. By "both" abiotic and biotic is meant stress which are caused by either biotic or abiotic factors, the effects of which can manifest in both physiological and biochemical effects resembling abiotic and biotic stress. Optionally, tolerance responses in crops to pathogenic nematodes and/or other pathogens may be enhanced. Optionally, the microbiota, macrobiota, flora and/or fauna may recognise, respond or utlize the composition or components therof by means of receptors, receptor-ligand systems, proteins, biochemical signalling or enzymes. Optionally, the microbiota, macrobiota, flora and/or fauna may recognise, respond or utlize the composition or components therof following the processing, partial breakdown, digestion, or biochemical modification of the components.

Optionally, the composition may be applied to the plant in accordance with the "diversified germination behaviour of seed population". By "diversified germination behaviour" means the difference in rate of germination in seed population observed due to difference in seed morphology and genetically controlled mechanisms involved in seed dormancy. Optionally, the first application may take place by means of fertirrigation or soil application, with first application taking place one week after sowing and at regular intervals subsequently thereafter, also by fertirrigation or soil application, with the total duration and timing of intervals dependent on the life-cycle characteristics of the particular nematode species targeted and the root growth, vegetative growth and/or reproductive growth of the crop in use. By "fertirrigation" (also referred to as 'fertigation) is meant the application of compositions, fertilizers or water soluble products through an irrigation system. Application of the composition may also be by chemigation. By "chemigation" is meant application of composition as a standalone, or as a tank mix with other fertilizer, chemical or bioformulations through irrigation systems. Application of the composition may also be via soil conditioners or soil amendments. By "soil application" is meant application of the composition to the soil as a standalone or mixing with fertilizers, directed sprayed or applied to the soil, side dress treatments, or other methods such as surface, gravity, drip, microject, sprinkle, minisprinkle, microsprinkle, hose-move sprinkle, overhead, furrow, flood, bubbler, open canal systems and pressured piped systems. By "regular intervals" means at points in time that are equally distant from each other, on a weekly basis, bi-weekly or monthly basis, etc, and can take place prior to infection, during infection and/or after infection. By "total duration" means the total period in time extending from the first application to final application to the crop. By "timing of intervals" means the regulation of application in order to achieve the desired effects in growth, performance or marketable grade. By "dependent on the lifecycle characteristics" of nematodes means the periods of time encompassing phases of dormancy, hatch, infection, reproduction, free-living or pre-parasitic phases in either the external environment or inside live or dead plant tissue or the parasitic phase inside the host. By "root growth" is meant the period in time in which root develop and grow, including stages of root primordium formation, root meristem formation, establishment of tissue systems, root elongation, root hair formation and all stages in which root size and/or dry matter increases. Optionally further, the composition may be applied by foliar application, with first foliar application taking place at 50% post-emergence, followed by applications who's total duration and timing depend on the life-cycle characteristics of the particular nematodes species targeted and the vegetative and reproductive growth of the crop in use. By "foliar application" is meant foliar directed spray of the composition as standalone or as tank mix with other fertilizers, chemicals, bio-formulations or treatments, directly to the leaves and/or vegetative components of the plant. By "post-emergence" means the stage between the emergence of a seedling and the maturity of a crop plant. By based on "the vegetative growth stage" means the period of time in which plant utilizes most of its metabolic energy for shoot emergence, stem and leaf growth, developing itself into a mature plant and/or further growth and development obtained thereafter throughout the mature phase of life. By based on "the reproductive growth stage" means the period of time in which plant utilizes most of its energy to produce its reproductive organs, resulting in the flowering and fruit formation.

Optionally, the composition may be applied to annual plants and/or the associated growth media from the duration of seed sowing to harvesting in one growing season. By "annual" is meant plants that go through a complete life cycle, from seed to seed, in one growing season. Optionally, the composition may be applied to biennial plants and/or the associated growth media throughout the two year life cycle. By "biennials" means plants that take two years to complete a life cycle. Optionally, the composition may be applied to perennial plants and/or the associated growth media at planting, growing, blooming, seeding and/or post-harvest periods for number of years. By "perennial" means plants that continue growing, blooming and seeding for a number of years. Optionally, the composition may be applied to the plant and/or the associated growth media at points in time either prior to the growing season, during the growing season, at the end of the growing season, just after the growing season, or outside of the growing season, such as during summer or winter off-season periods or periods of crop rotation. By "off season" is meant the practice of growing plants during periods of time outside of the optimal or normal growing season. Optionally, the composition may be applied to the growth media and/or plants, optionally including cool season crops, cover crops and/or turf grass. By "cool season crops" is meant plants that grow optimally at cool temperatures but are less tolerant to higher temperatures. By "cover crop" is meant plants grown for the protection and enrichment of the soil, optionally between regular periods of crop production. By "winter seeding", "spring seeding" and "summer seeding" is meant periods of time during the year when seeds are sown. By "frost seeding" is meant seeding performed at the end of winter when temperatures are above freezing during the day but may be below freezing at night. By "dormant seeding" is meant planting of seeds during time periods in which germination is unlikely to occur and the seed enters a dormancy period until conditions are optimal. By "overseeding" is meant the application of seeds directly onto existing areas of vegetation without disturbing the growth material, optionally, for the purposes of enhancing the health and thickness of the growth area. Optionally, the composition may be applied as a single application. Optionally, the composition may be applied as a treatment for the purposes of enhancing or maintaining quality, viability, shelf-life and/or to prevent storage or transport-related losses.

Definitions

β-glucans are homopolysaccharides of linear or branched glucose residues. β-(1,3) glucans are a naturally occurring class of polysaccharides found in many species of yeast (including Baker's Yeast or *S. cerevisiae*), mushrooms, plants (including cereals) and some bacterial, lichen and algal species (particularly brown algae or the *Ascophyllum* and *Laminaria* families). However, the structure and physiological properties of the glucans found in these sources is quite different with the beta glucans isolated from cereal sources (like wheat, barley and oats) being linear homopolysaccharides (of glucose) with approximately 70% (1,4)-linkages and 30% (1,3)-linkages (Cui et al, 2000 and MacGregor and Rattan, 1993), while the glucans isolated from yeast consists predominantly of β-(1,3) glucan chains with β-(1,6) branching as well as a small incidence of β-(1,6) linked chains. (Magnelli et al, 2002).

Algal β-glucans, called laminarin, consist of β-(1,3)-D glucan with occasional (1,6) linked branches. Laminarin from *Laminaria digitata* occurs as two homologous series of molecules, a minor G series containing 22-28 glucosyl residues and a more abundant M series consisting of 20-30 glucosyl residues linked to a mannitol residue. Laminarin from many species of *Laminaria* (including *Laminaria hyperborea*) is insoluble and consists of predominantly β-(1,3) chains while the laminarin from *Laminaria digitata* is soluble and consists of small but significant levels of β-(1,6) linked branches. (Read et al, 1996).

The β-glucans found in yeast are long linear chains of up to 1300-1500 residues of glucan molecules linked by a β-(1,3) bond with a minor incidence of β-(1,6) chains (which are much smaller and have only about 140 residues). Algal β-glucans on the other hand (also called laminarin) have much smaller chain lengths (average residue size of only 24 residues) with occasional β-(1,6) branches depending on the species. *Laminaria digitata* has the 1,6 branching which make the glucans derived from them water soluble. Other *laminaria* species like *hyperborea* do not have this branching which makes the linear chains aggregate and makes the glucans extracted from it, predominantly insoluble. Glucans may also be produced synthetically by means of chemical synthesis or biotechnological approaches.

Natural polysaccharides built up essentially of sulfated alpha-L-fucose residues are known as fucoidans (or α-fucans). These are present in brown algae, some echinoderms and are the predominant polysaccharide in brown seaweed, like *Ascophyllum nodosum* and the *Laminaria* spp. Fucoidans (α-fucans) have been extensively studied due to their diverse biological activities, since they are potent anticoagulant, antitumor, and antiviral agents. Fucans may also be produced synthetically by means of chemical synthesis or biotechnological approaches.

Mannitol is a sugar alcohol derived from mannose which can occur in the form of D-mannitol, it's epimer D-sorbitol or other isomeric forms. Mannitol is found in a wide variety of plants and seaweeds and may also be produced synthetically by means of chemical synthesis or biotechnological approaches.

By "glucan" is meant a polysaccharide molecule comprising at least two saccharide monomers, optionally D-glucose monomers, wherein each monomer is linked to an adjacent monomer by a glycosidic bond. The polysaccharide molecule may be linear or branched i.e. the polysaccharide molecule can be a straight-chain polysaccharide or a branched chain polysaccharide. Optionally, the glucan is a branched chain glucan. The glucan may be an alpha glucan or a beta glucan. Optionally, the glucan is a beta glucan. By "beta glucan" is meant a glucan comprising at least one beta glycosidic bond. A glycosidic bond is intended to mean a glycosidic bond, wherein a carbon atom of a first monomer forms a bond, optionally a single order bond, with a carbon atom on an adjacent monomer. A beta glycosidic bond is intended to mean a glycosidic bond, wherein a functional group, optionally a hydroxyl group, attached to a carbon atom of a first monomer extends above the plane of the monomer (equatorially). Optionally, the C1 carbon atom of a first monomer forms a bond, optionally a single order bond, with the C6 carbon atom on an adjacent monomer. Further optionally, the glucan comprises a beta (1→6) glycosidic bond, optionally an oxygen-containing beta (1→6) glycosidic bond. Optionally, at least one glucan is beta (1→3, 1→6) glucan. Still further optionally, the glucan is laminarin.

By "fucan" is meant a polysaccharide, optionally a sulphated polysaccharide, comprising at least two fucose saccharide monomers, wherein each monomer is linked to an adjacent monomer by a glycosidic bond. The polysaccharide molecule may be linear or branched. Optionally, the fucan is a branched fucan. The fucan may be an alpha fucan or a beta fucan. Optionally, the fucan is an alpha fucan. By "alpha fucan" is meant a fucan comprising at least one alpha glycosidic bond. A glycosidic bond is intended to mean a glycosidic bond, wherein a carbon atom of a first monomer forms a bond, optionally a single order bond, with a carbon atom on an adjacent monomer. An alpha glycosidic bond is intended to mean a glycosidic bond, wherein a functional group, optionally a hydroxyl group, attached to a carbon atom of a first monomer extends below the plane of the monomer (axially). Optionally, the C1 carbon atom of a first monomer forms a bond, optionally a single order bond, with either the C3 or C4 carbon atom on an adjacent monomer. Optionally, the fucan is fucoidan.

By 'mannitol' is meant a sugar alcohol derived from mannose, optionally D-mannitol or its epimer D-sorbitol, or other isomers of mannitol or other sugar alcohols.

Optionally, the glucan and/or the fucan and/or the mannitol is isolated from a brown alga, optionally brown seaweed. Optionally, the brown alga is a brown macroalga. Optionally, the brown macroalga, optionally brown seaweed, is selected from Phaeophyceae, optionally selected from Phaeophyceae Laminariales and Phaeophyceae Fucales. Further optionally, the brown alga, optionally brown seaweed, is selected from Laminariaceae, Fucaceae, and Lessoniaceae. Optionally, the brown macroalga, optionally brown seaweed, is selected from *Ascophyllum* species, optionally *Ascophyllum nodosum*, and *Laminaria* species, optionally *Laminaria digitata, Laminaria hyperborea, Laminaria saccharina, Laminaria japonica* or Sargassum species.

Alternatively, the glucan and/or the fucan and/or the mannitol is isolated from a red alga, optionally red seaweed. Optionally, the red alga is a red macroalga. Optionally, the red macroalga, optionally red seaweed, is selected from Florideophyceae, optionally selected from Florideophyceae Gigantinales, optionally selected from Gigartinaceae.

Alternatively, the glucan and/or the fucan and/or the mannitol may be derived by means of synthetic chemistry and/or biotechnology approaches.

Optionally, the composition may be applied at regular intervals to a plant by means of by means of fertirrigation or foliar spray.

Optionally, the plant is a flowering plant from the Angiospermae division. Further optionally, the plant is selected from families belonging to Solanaceae, Poaceae, Brassicacea and Amaranthaceae. By "Solanaceae" is meant the family of flowering plants which includes amongst others, species of potato (*Solanum tuberosum*), tomato (*Solanum lycopersicon*), pepper (*Capsicum* spp), eggplant (*Solanum melongena*), petunia (*Petunia hybrid*), tree tomato (*Cyphomandra betacea*), pepino (*Solanum muricatum*), naranjilla (*Solanum quitoense*) and coffee (*Coffea arabica*). By "Poaceae" is meant the family of monocotyledonous flowering plants which includes amongst others, species of maize, wheat, millets, rice, bamboo, common bentgrass, creeping bentgrass, velvet bentgrass and ryegrass. By "Brassicaceae" is meant the family of flowering plants which includes amongst others, species of *Brassica oleracea*,

*Armoraca rusticana, Brassica rapa, Brassica napus, Matthiola*, and *Raphanus sativus*. By "Amaranthaceae" is meant the family of flowering plants which includes amongst others, species of beetroot and spinach.

By "increasing growth, yield or marketable-grade" is meant increases in irreversible size of the plant and/or increases in amount harvested per unit area for a given time and/or increases in the levels of characteristics or quality-related criteria which provide increased return on investment. Moreover, growth includes increases in irreversible size of vegetative or reproductive plant organs selected from root, rhizoid, stem, leaves, flower, seed, fruit, cones, strobili or spores. By "growth media" means solids, liquid, water, gel, powder, soil, plant tissue or other materials which support the growth of plants and/or nematodes, and present in growth systems including outdoor fields, pots, greenhouses, hydroponic systems. Additionally, the growth media may refer to the plant tissue itself, in cases whereby the nematode feeds and/or spends part or all of part of its juvenile, and/or adult and/or reproductive life-cycle within the plant tissue, optionally leaf nematodes. By "levels comparable with DuPont™ Vydate® (oxamyl) and other registered nematicidal treatments" means increments in growth, yield or marketable-grade which are equivalent to those levels which are achieved by using commercially available chemical pesticides whose function is in killing plant-parasitic nematodes. The improvement in growth, yield or marketable-grade is intended to prevent or treat plant diseases symptoms associated with the presence of parasitic nematodes including, those manifesting at the root (root knots (galls), cysts, root lesions, root tip injuries, excessive branching of roots, stunted root systems), those manifesting above ground (overall decline of plant, yellowing of foliage, wilting, reduced numbers and size of leaves, reduced growth), those manifesting in stem and/or foliage and those manifesting at harvest and market levels (lower yield, lower marketable grade, lower quality). By "plant pathogenic nematodes", means parasitic species which infect plant tissues, optionally, root knot, cyst, stem, bulb, citrus, reniform, lesion, pin, stubby-root, sting, stunt, burrowing, lance, dagger, anguina, spiral, ring, sheath, sheathoid, seed gall, spring dwarf, summer dwarf, spine, sessile, awl, pine wood, needle, mint, foliar, leaf, false root knot or rice root nematodes, optionally belonging to the family Heteroderidae, Anguinidae, Pratylenchidae, Tylenchulidae, Hoplolaimidae, Trichodoridae, Belonolaimidae, Longidoridae, Criconematidae, Aphelenchoididae, Dolichodoridae or Parasitaphelenchidae, optionally belonging to the genus *Heterodera, Globodera, Meloidogyne, Ditylenchus, Pratylenchus, Tylenchulus, Rotylenchulus, Gracilacus, Trichodorus, Paratrichodorus, Belonolaimus, Merlinius, Quinisulcius, Tylenchorhynchus, Radopholus, Hoplolaimus, Xiphinema, Anguina, Helicotylenchus, Scutellonema, Mesocriconema, Hemicycliophoras, Hemicriconemoides, Aphelenchoides, Cacopaurus, Dolichodorus, Bursaphelenchus, Hirschmanniella, Longidorus, Aphelenchoides* or *Nacobbus*.

Optionally, the growth, yield or marketable-grade may be increased by enhancing tolerance to biotic stress.

Optionally, the growth, yield or marketable-grade may be increased by altering the plant substrate in the direction of decreased pathogenicity. Further optionally, the nematode food supply may be altered in accordance with the contents of the composition or through alterations imparted to the plant by the contents of the composition.

Optionally, the growth, yield or marketable-grade may be increased by favourably interfering with the nematode life-cycle in the direction of decreased pathogenicity. Further optionally, the life cycle stages affected include the embryonic stage, hatch stage, juvenile stages (J1-J4) and the adult stage.

Optionally, the growth, yield or marketable-grade may be increased by favourably interfering with nematode fecundity in the direction of decreased pathogenicity.

Optionally, the growth, yield or marketable-grade may be increased by favourably interfering with nematode population dynamics. Further optionally, population dynamics may be altered such that the male:female ratio changes in the direction of decreased pathogenicity, optionally with a higher proportion of free living nematodes than infectious and/or reproducing females. Further optionally, population dynamics of parasitic and/or non-parasitic species of free-living species of nematodes may also be favourably altered.

Optionally, the growth, yield or marketable-grade may be increased without requiring reductions in the numbers of nematodes present in the soil.

Optionally, increases in growth, yield or marketable-grade may be achieved by enhancing the overall soil, soil ecosystem, enhancing soil fertility, enhancing levels of soil biota and microbiota and/or lowering levels of other pathogens and/or pests. Further optionally, levels of soil biota such as free living nematodes and/or microbiota such as bacteria and fungi may be favourably altered in a direction which promotes plant health. Further optionally, the levels and/or success of infection or parasitism by pathogenic nematodes and/or other pathogenic species may be reduced. Further optionally, other pathogenic species may include species of fungi, oomycetes, bacteria, viruses, viroids, virus-like organisms, protozoa, insects, mites, aphids or nematodes. Further optionally, free living nematodes may include beneficial species which infect pest species, consume bacteria, are grazing species, predatory species, species which are classified as either colonizers and or persisters and/or other species which perform other important functions within the ecosystem. By 'colonizers' is meant free living nematodes with which are tolerant to disturbances, have short life cycles, high reproductive rates, which increase in numbers under favourable conditions and exhibit fluctuations in population density. By 'persisters' is meant nematodes with greater sensitivity to disturbances, lower reproductive rates, longer life cycles, lower dispersal capacities and which exhibit lower degrees of population fluctuation. Further optionally, soil microbiota may include beneficial species of fungi, oomycetes, bacteria, viruses, viroids, virus-like organisms, protozoa, insects or mites. Further optionally, nematode species may be favourably altered in the direction of ratios of pathogenic free living nematodes (PPN) to beneficial bacteria/fungal feeders which are conducive to enhancing plant growth. Further optionally, nematode species and/or population structure may be altered in the direction of favourable ratios of beneficial species of free living nematodes species as measured by colonizers/persister scales, maturity indices or species ratios or other measures. By 'microbiota' is meant species of bacteria, fungi or other microbes present on or within nematodes, within the soil, soil ecosystem and/or plants. Optionally, the bacteria or fungi are selected from species which reside within the intestinal tract of pathogenic and/or beneficial nematodes, optionally soil-derived gut bacteria, species which form part of nematode-bacterium symbioses, species present in eggs and/or cysts, species which form part of entomopathogenic nematode-bacterium complexes, species which influence nematode reproduction, nematophagous bacteria, rhizobacteria, endophytic fungi and/or soil bacteria or fungi which provide micro- and macro-nutrients in bioavailable forms. By 'nematophagous bacteria' is meant obligate or opportunistic parasitic bacteria, rhizobacteria, endophytic bacteria, parasporal Cry protein-forming bacteria and symbiotic bacteria. By 'rhizobacteria' is meant bacteria resident within the rhizosphere which can induce resistance in plants, i.e. induced system resistance. By 'endophytic fungi' is meant non-pathogenic root colonizing fungi and mycorrhizae which compete with other pathogens in roots and can also modify root exudates. Optionally, the microbiota may include species of algae, fungi, oomycetes, virus, viroids, virus-like organisms, protozoa or nematodes. Optionally, the microbiota are resident in the soil and/or are located in proximity to or resident within the rhizosphere and/or exert their effects on and/or within the rhizosphere. By 'rhizosphere' is meant the region in growth media or soil containing and/or influenced by microorganisms and/or root secretions. Optionally, the microorganisms and/or plant roots in the rhizosphere may secrete root border cells, root exudates, hatch stimulating agents, chemical attractants, repellents or other compounds.

Optionally, the microbiota influence nematode plant:host recognition and/or interactions, either directly or indirectly.

Described herein is a composition consisting of a formulation of laminarin and/or alpha fucans or at least one mannitol in combination with glucan and/or fucan that has altering effects on one or more of: (I) root length, (II) tuber weight, (III) tuber number, and (IV) marketable yield; whilst not causing a reduction numbers of pathogenic nematodes. In addition, we have demonstrated clear effects on growth, performance, yield and quality parameters which reach levels which are statistically indistinguishable from those achieved using commercial nematicides.

Accordingly in one aspect, the invention provides the use of a composition comprising beta-glucans and/or alpha fucans or at least one mannitol in combination with glucan and/or fucan in a method of improving plant growth and performance through application of the composition at key developmental and growth phases throughout the life-cycle. In preferred embodiments, beta glucan and alpha funcans and mannitol may be derived from more than one source which includes seaweeds and some echinoderms. The seaweed may be derived from the group which consists of Laminariaceae, Fucacea, Gigartinaceae or Lessoniaceae. Optionally, the glucan, fucans and/or mannitol may be derived by means of chemical synthesis of biotechnological approaches.

Also described are:
an application regimen for preventing or treating disease symptoms in plants such as those selected from families belonging to Solanaceae, Poaceae, Brassicacea and Amaranthaceae by applying to the plant during key developmental or growth periods, a composition comprising beta-glucans and/or alpha-fucans or at least one mannitol in combination with glucan and/or fucan.
an application regimen for improving plant growth, performance and marketable yield by applying to the plant during key developmental or growth periods, a composition comprising beta-glucans and/or alpha-fucans or at least one mannitol in combination with glucan and/or fucan.
an application regimen for enhancing tolerance to biotic and abiotic stress, by applying to the plant during key developmental or growth periods, a composition comprising beta-glucans and/or alpha-fucans or at least one mannitol in combination with glucan and/or fucan.
an application regimen for interfering the nematode life-cycle, fecundity, development or digestive system in the direction of decreased pathogenicity, by applying to the plant or soil or growth media during key developmental or growth periods, a composition comprising beta-glucans and/or alpha-fucans or at least one mannitol in combination with glucan and/or fucan.
an application regimen for interfering with nematode population dynamic, both non-pathogenic species and pathogenic species, by applying to the plant or soil or growth media during key developmental or growth periods, a composition comprising beta-glucans and/or alpha-fucans or at least one mannitol in combination with glucan and/or fucan.
an application regimen for favourably altering soil microbial dynamics in different growth environments by applying to the plant or soil or growth media during key developmental or growth periods, a composition comprising beta-glucans and/or alpha-fucans or at least one mannitol in combination with glucan and/or fucan.

The application regimen for administration of the composition may be on a weekly basis at a rate of approximately 60 grams of bioactives applied per hectare of growing area. The application regimen may be adapted to apply the composition at higher levels, approximately 10-fold per hectare, in order to provide greater yield, marketable grade and return on investment.

The composition comprising beta-glucans and/or alpha fucans or at least one mannitol in combination with glucan and/or fucan described herein may be used in a method:
for increasing root length,
for increasing tuber weight,
for increasing tuber number,
for increasing performance,
for increasing marketable yield,
for achieving the above without posing a risk to the ecosystem or user
for influencing nematode multiplication rate, reproductive, digestive or life-cycle parameters.
preventing or treating disease symptoms in plants such as those selected from classes of Gymnospermae or Angiospermae, optionally those families belonging to Solanaceae, Poaceae, Brassicacea and Amaranthaceae, by applying to the plant during key developmental or growth periods with a composition comprising beta-glucans and alpha-fucans,

BRIEF DESCRIPTION OF THE DRAWINGS

The invention will be more clearly understood from the following description of an embodiment thereof, given by way of example only, with reference to the accompanying drawings in which.

DETAILED DESCRIPTION

Figure 1:
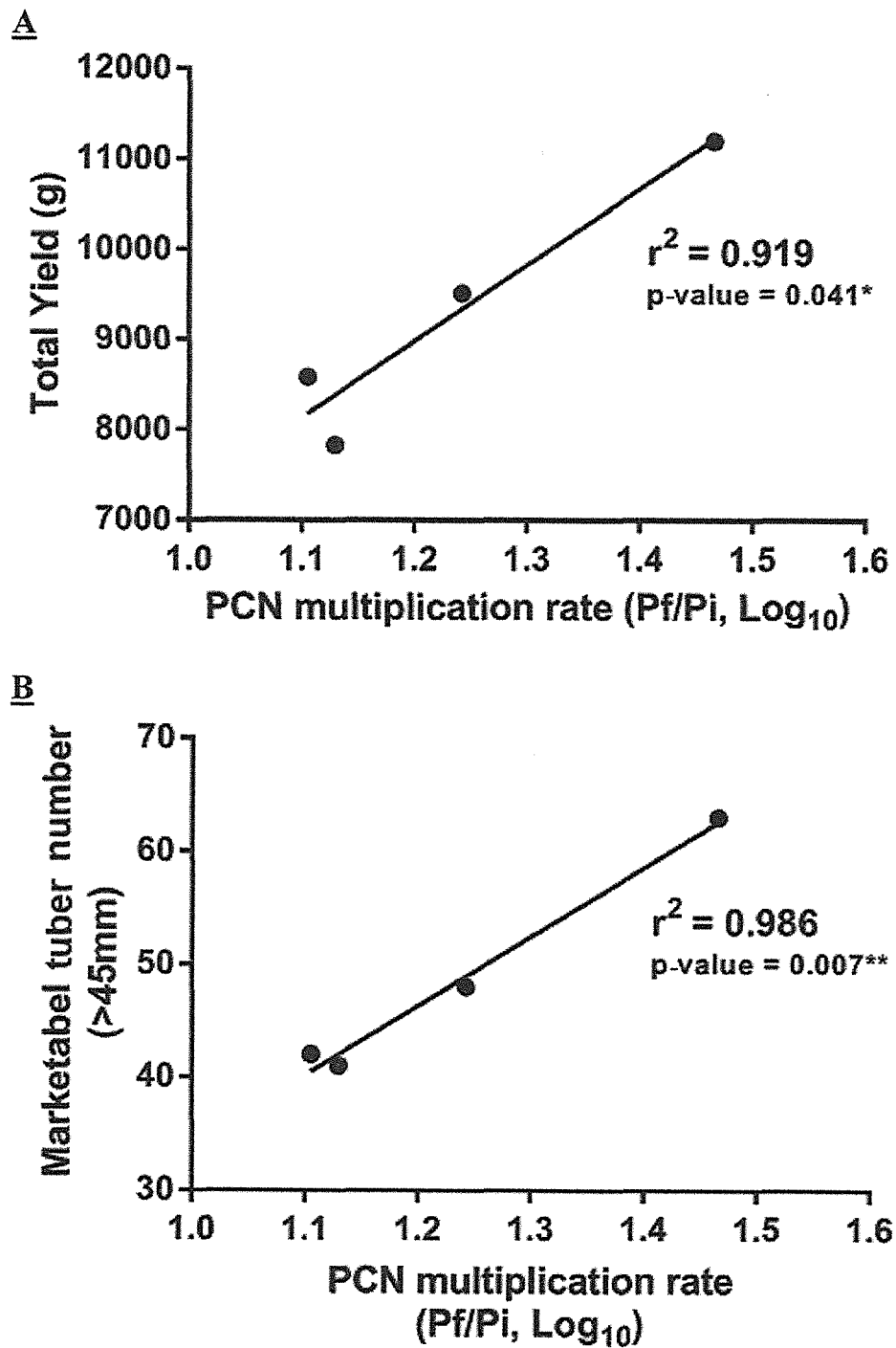
FIGS. 1 A and B are graphs illustrating the positive relationship between Potato Cyst Nematode (PCN) numbers and potato yield and marketable grade following application of Composition 2.

We describe a composition which is shown to improve growth, yield and marketable-grade of plants grown in media infested with plant-pathogenic nematodes, to levels comparable with those otherwise achieved through treatment with nematicide alone. Moreover, this composition is naturally-derived and shown not to be nematicidal, as nematode population numbers are not significantly reduced by the composition. Hence, this invention provides a natural, effective, safe alternative and economically viable means of enhancing the growth and yield of crops grown in a nematode infested growth media.

Seaweed Extracts

There is considerable interest in the possible plant health and growth promoting properties of seaweed extracts (Russo 1990 and Chojnacka et al., 2012). Evidence suggests that a number of compounds from seaweed may improve plant growth in the presence of nematodes. For example, some studies indicate that seaweed extracts can increase growth of Arabidopsis thaliana and tomato, while in some cases also impacting on nematode populations (Wu Y et al., 1998; Featonby-Smith B. C. and Van Staden J. et al.; 1983; Crouch et al. 1993A; Whapman et al., 1994). These effects are frequently attributed to the presence of compounds such as betaines and growth hormones such as cytokinins and auxins (Wu Y et al., 1998, Crouch and Van Staden 1993B, Stirk and Van Staden, 1997, Jenkins T et al., 1998). However, the levels of growth hormones in extracts of seaweeds used in these studies are often unclear, as methodologies used are frequently based on bioassays of growth hormone effects rather than taking direct quantitative measures (e.g. mung bean rooting bioassay). This approach is still widely applied today, despite its inherent limitations.

Also emerging from these early studies was an apparent impact of seaweed extracts on nematode fecundity. A study on tomato plants by Whapham et al., (1994) demonstrated reductions in the number of eggs produced by Meloidogyne javanica females after one generation post-treatment with a commercial extract of Ascophyllum nodosum, 'Maxicrop'. Further study by this group demonstrates a reduction in J2 numbers on treatment with this product, effects which they attribute to the betaine components of seaweed (Wu et al., 1997). However, much of this work was performed in laboratory conditions, for example, hatching of eggs in beakers containing seaweed media or water at a temperature of 20° C., and inoculation of plant with the second-stage juvenile (J2) infective stage. Furthermore, the 'Maxicrop' ash treatment also gave rise to significant reductions in J2, 63 days post-inoculation, which was not explained (Wu et al., 1997). Reductions in the number of Meloidogyne javanica females and egg recovery from plants treated with an extract of A. nodosum was reported by Wu et al., (1998) and attributed to levels of betaines in the composition. However, this study was carried out on Arabidopsis thaliana under controlled conditions. As the authors contend, these effects may be insufficient under normal agricultural conditions and furthermore, would have to be incorporated into other control measures, such as nematicides (Wu et al., 1998). Such studies are limited by several factors, such as a lack of comparison with commercial-grade nematicides, and in some cases, conclusions are based on findings from in-vitro work, effects which may not be observed in vivo, or in field conditions.

Other approaches to examining effects of seaweeds on fungi and nematodes involve extraction with solvents including n-hexane, chloroform and methanol and ethanol. Sutlana V et al., 2008 demonstrate an effect of solvent (n-hexane, chloroform and methanol) and ethanol extracts of seaweed on increasing mortality of Meloidogyne javanica juveniles, while also suppressing infection of chilli roots in screen-house experiments and field plots. Nematicidal and antifungal effects of such extracts have also been attributed to oily fractions containing various fatty acid esters, obtained through ethanol extraction (Ara J et al., 2005). However, the potential for extraction agents to account for some of these effects may be significant, for example, methanol is known to enhance crop growth and performance (Nonomura et al., 1992, Li, Y et al., 1995). Furthermore, the effectiveness of these extracts have not been examined in large-scale trials and compared with current and effective commercial nematicides. While Sutlana V et al., 2011, report an effect of Solieria robusta, on reducing nematode gall numbers to levels similar to carbofuran, dried seaweed was used. Properties of dried seaweed meal are highly variable both regionally and between species and without clearly defined extraction procedures, it may be difficult to standardise or even repeat such effects. Indeed, many of the early studies into seaweed and crop growth in presence of nematodes have not been repeated. Where positive results have been found, extracts from a large number of species have been shown to be ineffective (Paracer S et al., 1987) and in some cases, extracts are found to negatively affect plant growth and reduce tolerance to nematode attack (De Waele D et al., 1988). Recent efforts have also failed to identify an extract of seaweed which can provide the protection and yield increases to levels otherwise achieved by commercial nematicides (Martin T J et al., 2007). Thus, there remains no seaweed-based composition to-date which can provide benefits to crops to levels currently achieved through use of registered nematicides.

In conclusion, while the evidence from the 1980s to present day suggests that seaweeds may promote plant growth in the presence of nematodes, 30 years have passed without an effective or viable seaweed-based alternative to the use of commercial nematicidal treatments being developed. In spite of their dangers to the environment and other hazards, commercial chemical-based nematicides remain the only practical method of counteracting the effects of nematode infestation on crop performance. For a natural alternative to nematicides to be viable in agriculture, it must demonstrate effects which reach equivalence to or greater to those achieved using commercial nematicides alone. The lack of safe and viable alternatives to use of dangerous nematicides is addressed by the present invention.

Laminarin, Fucoidan and Mannitol

The effects of polysaccharides derived from brown algae in enhancing plant performance in nematode infested grounds, particularly laminarin, fucoidan and mannitol, have not been explored. In mammals, there is considerable evidence to support a role for laminarin and fucoidan in enhancing various physiological and immunological parameters (Reilly et al., 2008, Novak et al., 2009, Leonard S G et al., 2011A and 2011B, Smith et al., 2011). There are also studies which suggest a role for glucans in eliciting plant defence responses (Klarzynski O, et al., 2000 and references therein, Wolskia et al., 2006). Also, mannitol has also been cited for use in osmotic priming (Dursun et al., 2012), However, these findings cannot be extrapolated to plant-parasitic nematodes. Besides the obvious differences between animal and plant morphology and physiology, findings relating to plant responses to bacteria, fungal and viral pathogen do not necessarily to apply to Animalia such as nematodes or insects. In particular, the processes involved in parasitism between nematode and plant host contrasts with mechanism employed by other pathogens. For example, several species of nematodes must transform root cells into feeding sites (syncytia), a process requiring the secretion of a complex array of effector proteins, the roles of which are still being elucidated (*Hamamouch* N et al., 2012). Thus, while induction of SARs may provide benefits against certain bacterial or fungal pathogens, defensive responses to nematodes are likely to be considerably more complex. Indeed, a study by Chinnasri B et al., (2006) shows that SAR inducers varied in their ability to reduce nematode reproduction on pineapple, with variation in potency likely due to different activation points along the signal transduction pathway of SAR. While acibenzolar showed a broader spectrum of control than BABA and riboflavin, increases in crop yield were not achieved, rather, adverse effects in pineapple growth were reported (Chinnasri B et al., 2006). Also, while early studies indicate that plant growth promoting rhizobacteria (PGPR) may be used in inducing systemic resistance in plants against pests and diseases (Ramamoorthy V et al., 2001 and references therein), these approaches have had limited success with nematodes.

Overall, the effectiveness in using elicitors of systemic resistance in plants against nematodes is poorly understood. There are no known inducers of systemic resistance in plants which can provide benefits to crops to levels currently achieved through use of registered nematicides. While glucans are known elicitors of plant defence, it is unclear if such properties impart effective responses against nematode infestation or whether or not significant increases in crop performance can be achieved. Indeed, while recent attempts to develop compositions which are effective against nematodes have made reference to glucans as elicitors of plant defence (US 2009/0104222 (also published as EP2012591A2), EP1135026 A4 (also published as U.S. Pat. No. 6,582,961), US 2002/0004458 A1, U.S. Pat. Nos. 7,927,635 and 8,246,965), in no instance do glucans represent the active component of these compositions. Rather, glucans are generally cited merely as 'enhancers' for the composition being described. Thus, there has been no disclosure to date on the use of laminarin or fucoidan (or related glucan or fucan) or mannitol compounds as active ingredients in enhancing plant performance parameters in nematode infested grounds, nor is there any evidence of such effects reported in the scientific literature to date.

A suitable source of the active ingredients in the compositions described herein is seaweed, in particular, species of brown algae. Methods of producing laminarin with anti-cancer application are disclosed in US 2003119780, US 20050065114 and US 20050095250, via extraction from seaweed as the raw material or by means of synthesis of anaologues. The method of extraction typically involves acid hydrolysis followed by centrifugation and then ultra-filtration, thereby giving rise to a purified fraction of laminarin. Species of seaweed such as *Laminaria digitata* contain water soluble forms of laminarin, thus negating the use of solubilisation steps in this process.

For the compositions of the invention, there is no requirement for a specific conformation of laminarin/glucan as its three-dimensional conformation is not deemed to determine it mode of action, but rather the length of the chain and the nature of the bond. In some cases there is not a requirement for the laminarin to be separated from other algal sugars such as fucoidan or sugar alcohols such as mannitol, as these molecules impact distinct biological actions of their own and act in synergy with laminarin to enhance plant performance in the face of pathogenic challenge.

The distinctive nutritional characteristics of seaweed includes a category of nutrients called sulphated polysaccharides. These are carbohydrate-related nutrients, also referred to as fucans, have been examined for their properties in mammals, of which include anti-inflammatory properties and inhibition of human complement activation in vitro (Blonden et al., 1995). Biological properties of these molecules in plants are unclear.

The immunological properties of laminarin, both in its naturally extracted and synthethic form, have been investigated extensively. US2005095250, US 20030119780, US 20050065114 and US 20040127457 discuss anti-cancer and anti-inflammatory properties of laminarin. Since the 1970s, β-glucans have been recognised as playing a role plant-pathogen interactions. In modern times, elicitor properties of glucans has also been demonstrated in tobacco plants (Klarzynski O, et al., 2000 and references therein) and Wolskia et al., (2006) found an enhancement in protection conferred against *Fusarium solani* f. sp. *eumartii* and *Rhizoctonia solani* AG3 in plants and tubers. However, the extract used by Wolskia et al., 2006 was from a *rhizoctonia* isolate and it is difficult to extrapolate studies on fungi to organisms such as nematodes. As discussed herein, plant defence responses which are effective against one pathogen do not necessarily indicate effectiveness against another. Nor do defensive responses which are effective against nematodes necessarily correspond to increases in crop growth. While U.S. Pat. No. 5,750,472 disclose the use of laminarin in seed germination, there is no disclosure on plant growth and performance in the presence pathogenic nematodes.

The use of β-glucans or α-fucans or mannitol, singly or in combination for improved plant performance and marketable grade is not taught or suggested by the prior art. Furthermore, none of the above references refer to the use of β-glucans or α-fucans or mannitol, singly or in combination for use in enhancing tolerance to biotic stress, altering food supply or favourably interfering with the nematode life-cycle, fecundity, development or digestive system in the direction of decreased pathogenicity. Nor do they refer to the benefits of mannitol, β-glucans or α-fucans, particularly those derived from seaweeds, as a means to improving plant growth, performance and marketable grade in nematode infested ground and act as replacements for registered, commercial nematicides.

The invention will be more clearly understood from the following examples.

EXAMPLES

The examples given are the results of investigative research on the effects of compositions containing laminarin, fucoidan and mannitol on potato and grass species in the face of challenge against *G. pallida* (cyst nematode) and *Meloidogyne minor* (root knot nematode), as a model for all flowering plants including families belonging to Solanaceae, Poaceae, Brassicacea and Amaranthaceae and all plant parasitic nematode species including families belonging to Heteroderidae, Anguinidae, Pratylenchidae, Tylenchulidae, Hoplolaimidae, Trichodoridae, Belonolaimidae, Longidoridae, Criconematidae, Aphelenchoididae, Dolichodoridae or Parasitaphelenchidae. The examples shown include field trials carried out on potatoes using seaweed extract containing laminarin, fucoidan and mannitol in combination in two compositions, Composition 1 and Composition 2. Fucoidan is also examined individually. In addition, glucan-alone, mannitol-alone, glucan+fucan, glucan+mannitol and fucan+mannitol are also examined as separate treatments. Comparisons with a commercially available nematicide, namely DuPont™ Vydate® (oxamyl) is also provided.

Example 1

Aims: To develop a composition for use in increasing growth, yield or marketable-grade of plants grown in media or soil infested with plant-pathogenic nematodes, to levels comparable with DuPont™ Vydate® (oxamyl).

Materials and Methods:

Field trials were undertaken in 2008, 2009, 2011 and 2012 on soils known to contain pure *Globodera pallida* cyst nematode populations. Free living species of pathogenic nematodes are also known to be present within these soils, including the genera: *Heterodera/Globodera* (cyst), *Pratylenchus* (lesion), *Rotylenchus* (spiral), *Tylenchus, Tylenchorhynchus* (stunt), *Paratylenchus* (pin), *Helicotylenchus* (spiral). The trials were designed to examine the efficacy of compositions containing glucan, fucan and mannitol, in enhancing potato tuber yield and marketable grade as compared with a commercial nematicide, Vydate, and untreated controls. In each trial, the forms of glucan and fucan used were laminarin and fucoidan respectively. The optimal application rates and bioactive content of the compositions required to achieve these targets was determined throughout the five year field trial period. Each treatment was fully randomized within four plots. Each plot contained six 0.7 m wide drills with a length of 4.0 m in 2008 and 3.7 m in 2009, 2011 and 2012. Twelve tubers per drill were planted at 33 cm spacing in May of 2008 and 2011 and in the first week of June in 2009 and 2012. The cultivar Navan, (*Solanum tuberosum* L. ev. Navan) planted in 2008, 2011 and 2012 with Désirée planted in 2009. The four centre drills were used for data collection with outer drills serving as guard rows. Compositions were applied by foliar spray at 50% post-emergence and at approximately seven day intervals thereafter. Foliar spray was stopped after senescence was noticed and crops harvested in autumn. Compound fertilizers and fungicides were also applied at recommended rates and intervals, the latter in order to prevent against potato blight, *Phytophthora infestans*.

In the 2008 trial, two compositions (Composition 1 and 2) were applied at a rate corresponding to a bioactive ratio of 1:2:3 of laminarin:fucoidan:mannitol. The application rate of bioactives per hectare was 73 g for Composition 1. The rate of bioactives applied in the Composition 2 treatment, termed 'Composition 2A', corresponded to a total of 67 g per hectare. Composition 1 was selected for a replicate trial in the following year on the basis of increased performance over Composition 2 in 2008. The bioactive ratio of Composition 1 was maintained at a standard ratio of 1:2:3 in 2009 and in all future trials in which Composition 1 was assessed. In the 2009 trial, Composition 1 was applied according to the same rate and bioactive ratio as in 2008. However, as Composition 1 did not provide benefits comparable to Vydate in 2009, further experiments were undertaken in the laboratory setting in 2010, with the aim of examining the potential benefits associated with increasing composition application rates (see Example 2).

Application rates and bioactive content of the compositions were increased and examined in a field trial in nematode infested grounds in 2011. For Composition 1, the application rate was increased 2.5 fold compared to 2008, corresponding to 182.5 g/Ha, according to the same bioactive content and ratio as in 2008. The total bioactive content of the Composition 2 treatment in the 2011 trial, termed 'Composition 2B', was increased from 2008 to achieve an application rate of 410 g of bioactives per Ha. Composition 2B represents a re-formulated version of Composition 2A used in 2008, being applied according to a ratio of 1:1:2 of laminarin, fucoidan and mannitol rather than a ratio of 1:2:3. A further trial was undertaken in 2012 to examine the reproducibility of the increases achieved over Vydate® with Composition 2 in 2011. Composition 1 was also included in the trial, according to the same bioactive rates and ratio as in 2011. In 2012, the bioactive ratio of Composition 2 was adjusted and applied according to a ratio of 1:1:3 of laminarin, fucoidan and mannitol rather than 1:1:2 in the previous year. This corresponded to an application of 493 g of total bioactives per hectare (termed 'Composition 2C'). Additionally, seed treatment with Composition 2C was assessed in 2012 which involved the application of a solution containing the composition to the seed potatoes and allowing to dry before planting. Planting took place within 24 hours of drying.

In each trial, application of the foliar sprays were stopped after senescence was noticed as beginning to occur. Each block was comprised of:

1. Control 1: A fallow plot where no plants were grown or allowed to grow
2. Control 2: A plot planted with potatoes but without any treatment.
3. Control 3: A plot with the nematicide 'Vydate' (Oxamyl) incorporated into the soil at full rate and planted with potatoes.
4. Potatoes planted and Composition 1 foliar spray applied.
5. Potatoes planted and Composition 2 foliar spray applied.*

*Composition 2 was not assessed in 2009.

The harvested tubers were graded according to size as follows in 2008 and 2011: <45 mm: small, table potato grade; 45-65 mm: Table potato grade; >65 mm: Large baking type grade potatoes. The numbers and weight of tubers were recorded for each grade, with "marketable yield" defined as tubers (weight and number) which fall into the >45 mm category. In the 2012 trial, a similar grading system was used: <35 mm, 35-55 mm and >55 mm; with the >35 mm category defining "marketable yield". The potential impact of applications on Potato Cyst nematode (PCN) numbers was also examined. This involved the collecting of soil samples from each plot immediately before planting to calculate the initial PCN population (Pi). This was repeated on the day before harvesting, giving the final population density (Pf). The PCN were extracted from the soil using a standard protocol for the 'Fenwick Can' process. The number of cysts per gram of soil and the number of eggs per cyst were calculated, thereby giving the number of PCN eggs per gram of soil for both pre planting (Pi) and pre harvest (Pf). These figures were then used to calculate the multiplication rate of the nematode (Pf/Pi). One-way ANOVA was used to test for differences between groups. Linear regression analysis was used to determine the correlation between PCN on yield parameters.

Results:

Performance and Marketable Grade

In the initial field trial in 2008, Composition 1 significantly increased the total yield per plot compared to untreated controls (22444 g versus 19334 g, p-value=0.018*, Table 1), while increases achieved with Composition 2A (21488 g) were not statistically significant. Treatment with Composition 1 was also associated with a significant increase in marketable yield versus controls (21091 g versus 18055 g, p-value=0.029*). Both Composition 1 and 2A were associated with significant yield increases in the 45-65 mm marketable grade category (11253 g and 11438 g) compared to untreated controls (8094 g; p-values 0.027 and 0.021* respectively). Composition 2A also significantly increased numbers of tubers/plot in the 45-65 mm category compared to untreated controls (n=83 versus 60, p-value=0.031*). In contrast to Composition 1 and 2A, application of Vydate® (oxamyl) did not increase yield or marketable grade of potatoes. This was attributed to the high levels of rainfall occurring during this season, a factor known to limit the effectiveness of this nematicide. In conclusion, Composition 1 enhanced both total yield and marketable grade to levels greater than Vydate® or untreated controls, while Composition 2A achieved increases in marketable grade but not in total yield. On the basis of increased performance over Composition 2A, Composition 1 was therefore selected for a second trial in 2009.

In 2009, a substantial increase in average yield per drill was achieved on treatment with Composition 1 compared to untreated controls (5528 g versus 3801 g, p-value=0.052, Table 2), corresponding to a 45% increase in yield over control. In contrast however, Vydate® (oxamyl) was associated with a considerably higher total increase in yield over controls (12817 g versus 3801 g, p-value>0.0001****). This trial confirmed that application of Composition 1 is associated with enhancements in potato yield on nematode infested ground. However, given the failure to provide increases in yield to levels comparable to Vydate®, the application rates and bioactive content of the composition were re-examined in the laboratory setting in 2010 (see Example 2) and adjusted thereafter to enhance efficacy ahead of the forthcoming field trial planned for 2011.

The aims of the 2011 trial were to examine the potential impact of increased bioactive application on enhancing yield and marketable grade as compared to Vydate® (oxamyl). In this trial, application of Composition 2B alone achieved an increase in average yield per drill statistically indistinguishable to that achieved with Vydate® (9284 g versus 10556 g, p>0.05) and representing a substantial 37% increase over untreated controls (6775 g, p-value<0.011*, Table 3). Increases in overall marketable yield (>45 mm tuber size) were also achieved with Composition 2B to levels comparable to Vydate (7888 g versus 9342 g, p-value>0.05) and significantly higher than untreated controls (7888 g versus 5349 g, p=0.006**). Significant increases in the overall numbers of higher marketable grade potatoes (>45 mm) were achieved with Composition 2B compared with untreated controls (n=49 versus 35, p-value=0.026*), statistically indistinguishable to Vydate (n=56). While Composition 1 also achieved increases in the numbers of high marketable grade potatoes (47 versus 35, p-value=0.049*; Table 3), it was not associated with increases in total yield to levels comparable to Vydate. Composition 1 was associated with an increase in total yield versus controls (7664 g versus 6775 g), however this did not reach statistical significance and was substantially less than that achieved with Vydate® (10556 g).

In conclusion, this trial demonstrates that treatment with Composition 2B is associated with significant increases in yield and marketable grade to levels comparable and statistically indistinguishable to Vydate® (oxamyl). The effectiveness of Composition 2 alone in enhancing yield and marketable grade to levels comparable to Vydate® was examined again in the field trial setting in 2012.

In 2012, application of Composition 2C was associated with significantly higher yield per drill than untreated controls (6695 g versus 4929 g, p-value=0.001**; Table 4), with increases statistically indistinguishable to those achieved Vydate® (6695 g versus 6479 g respectively, p-value>0.05). Likewise, overall marketable yield (>35 mm) per drill was significantly increased on treatment with Composition 2C compared to untreated controls (6449 g versus 4654 g, p-value=0.001*) and to levels comparable to Vydate (6300 g). While Composition 2C had no effect on low and middle marketable grade, a substantial increase in the large weight grade category (>55 mm) was achieved over controls (4571 g versus 2780 g, p-value=0.001*) and to levels comparable to Vydate (4551 g). This effect was also observed at the level of tuber number (p-value=0.004). Composition 1 did not increase yield or marketable grade significantly over untreated controls. However, Composition 1 was associated with a significant increase in yield in the lowest weight category both in terms of tuber number (n=19 versus 13, p-value=0.009) and weight (<35 mm; 383 versus 274, p-value=0.014*; Table 4). Seed treatment with Composition 2C was also associated with a marginal total increase in yield over control and slight increase within the 35-55 grade.

Overall, the findings of the 2012 trial demonstrate a significant increase in total yield and marketable grade on application of Composition 2, statistically higher than untreated controls and to levels comparable and statistically indistinguishable to those achieved with Vydate. Since similar effects were achieved in the trial undertaken the previous year, the effectiveness of Composition 2 on enhancing overall performance and marketable grade to levels comparable to Vydate, are shown to be reproducible. Overall, increases in yield and marketable grade were observed to be largely associated with the levels of bioactives applied per hectare. While application of 67-73 g/Ha is shown to be effective in enhancing yield and marketable grade (2008 trial) and also increased total yield in 2009, composition efficacy was enhanced at higher rates of bioactive application (2011 and 2012 trials). This is in line with observations from laboratory experiments showing the substantial effects of these type of compositions when applied at higher levels (see Example 2).

Potato Cyst Nematode (PCN) Populations:

Increases in tuber yield are achieved with compositions without negatively impacting upon nematode population numbers as demonstrated in Table 5. The multiplication rate of PCN (Pf/Pi) was not significantly affected on treatment with either Composition 1 or Composition 2 (Table 5). In contrast, treatment with nematicide (Vydate) is associated with a significant reduction in the nematode multiplication rate compared to untreated controls (Pf/Pi=0.62 and 17.28 respectively, p-value<0.05; Table 5), to levels similar to the fallow treatment. While a reduction in Pf/Pi was observed through use of Composition 1 in 2011 this was not significantly lower than untreated controls (7.04 versus 17.28, p-value>0.05, Table 5). Thus, in contrast to nematicide treatment, Compositions 1 and 2 do not significantly reduce nematode numbers. This demonstrates that the compositions do not act as nematicidal treatments when enhancing in crop growth and marketable grade. Moreover, in the case of Composition 2, drills with the highest levels of PCN were also associated with the greatest increase in overall yield and numbers of high-grade marketable tubers ($r^2$=0.919, p-value=0.041*, and $r^2$=0.986, p-value=0.007**, respectively, FIG. 1). This shows that Composition 2 achieves increases in yield and marketable grade without reducing parasitic nematode numbers, and moreover, is highly effective in the plots containing high levels of PCN.

Figure 2:
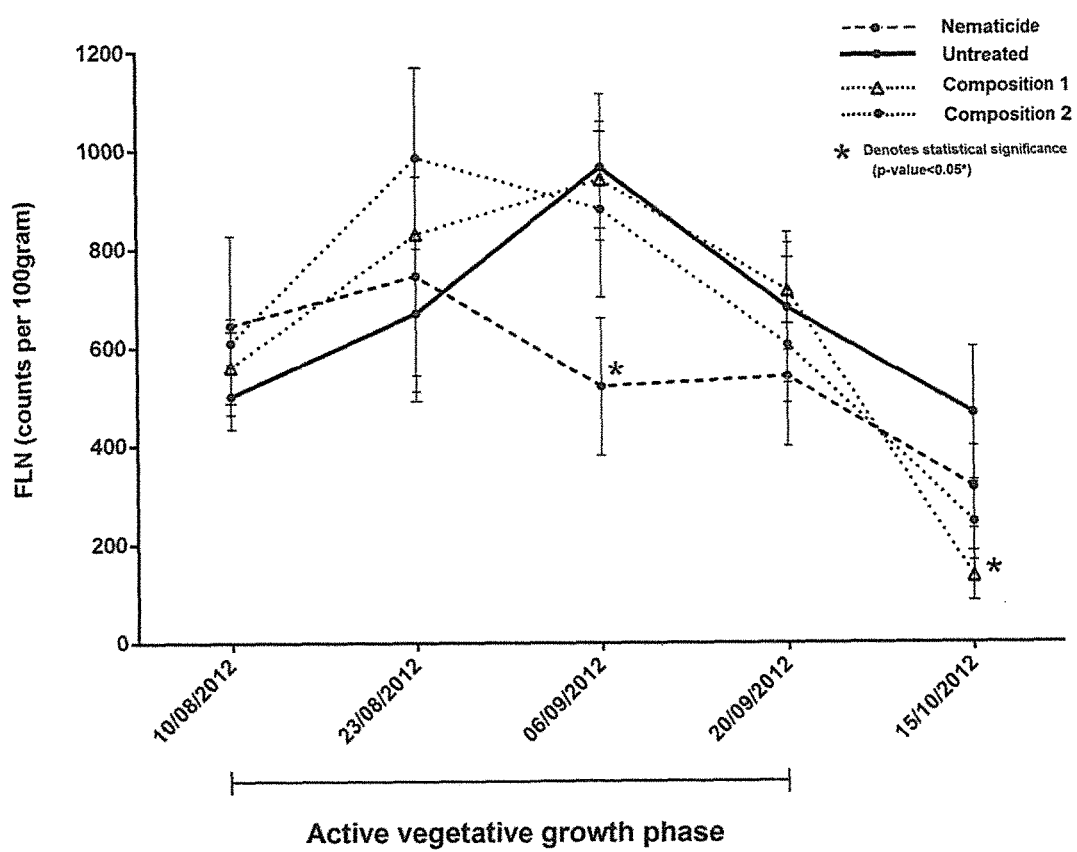
FIG. 2 is a graph which illustrates the population dynamics of free living nematodes (FLN) throughout the growing period for each composition.

Free Living Nematodes (FLN):

In 2012, the effect of compositions on free living nematode (FLN) was examined throughout the growing period. Plots were assessed for counts of FLN at selected time points. Nematicide treatment was associated with significant reduction in FLN counts compared to the untreated control during the growth phase (p-value<0.05, FIG. 2). In contrast, Composition 1 and Composition 2C were associated with FLN counts similar to the untreated control throughout the crop growth phase. This demonstrates that the Compositions do not negatively affect the overall soil ecosystem (FIG. 2). FLN counts were reduced for all treatments and the control close to harvest.

Discussion

These trials demonstrate that treatment of potatoes with Composition 2 is associated with significant increases in total yield and marketable grade, to levels comparable with a commercial nematicide DuPont™ Vydate® (oxamyl). In contrast to Vydate® (oxamyl) these increases were achieved without reducing nematode population numbers or having the nematicidal effects as are typically required in order for most commercial nematicides to be effective. In this manner, Composition 2, provides a means of enhancing agricultural output in the face of pathogenic nematode infestation. Composition 1 and 2 were also effective in non-favourable weather conditions known to otherwise negatively impact on the efficacy of commercial nematicides, such as the very high levels of rainfall which occurred in 2008, In contrast to commercial nematicides, Composition 1 and 2 do not posing any health risk or hazard to the individual applying the composition nor does they pose a danger to bees or harming bee populations. Furthermore, Composition 1 and 2 do not negatively affect the soil ecosystem.

Optimal Rates of Application:

Initial field trials demonstrated that the compositions could reach a level of efficacy equivalent to nematicide when applied at a rate of ≥67 g of bioactives per Ha (Composition 1 and Composition 2A). Therefore, 67 g represents the lower limit in which efficacy can be obtained from the compositions. However, ≥67 g/Ha did not produce reproducible results in the following year. By applying bioactives at a total rate of ≥400 g/ha, reproducible results comparable with nematicide were achieved in the 2011 and 2012 trials (Composition 2B and 2C). Overall, these trials indicated that while efficacy can be achieved at minimum rate of between 67 g/ha, higher rates of ≥400 g of bioactives per ha is required to ensure consistency year-on-year and achieve maximal yields. The higher rate of ≥400 g/ha refers to either the sum total of all three bioactives together, the sum total of dual synergistic combinations of the bioactives or the amount applied per hectare when applying the bioactives as individual, singular applications. While increases in yield can be achieved at a ratio of 1:2:3 of laminarin:fucoidan: mannitol (Composition 1 and 2A), a ratio of between 1:1:2 and 1:1:3 (Composition 2B and C respectively) achieves consistent increases in yield year-on-year.

In conclusion, application of Composition 2 was associated with significant increases in yield and marketable grade in nematode infested soils, to levels comparable with nematicidal treatments, but without requiring direct nematicidal effects. The differences in efficacy between Composition 1 and Composition 2 points to differences in the levels of bioactives present in the two compositions.

Figure 3:
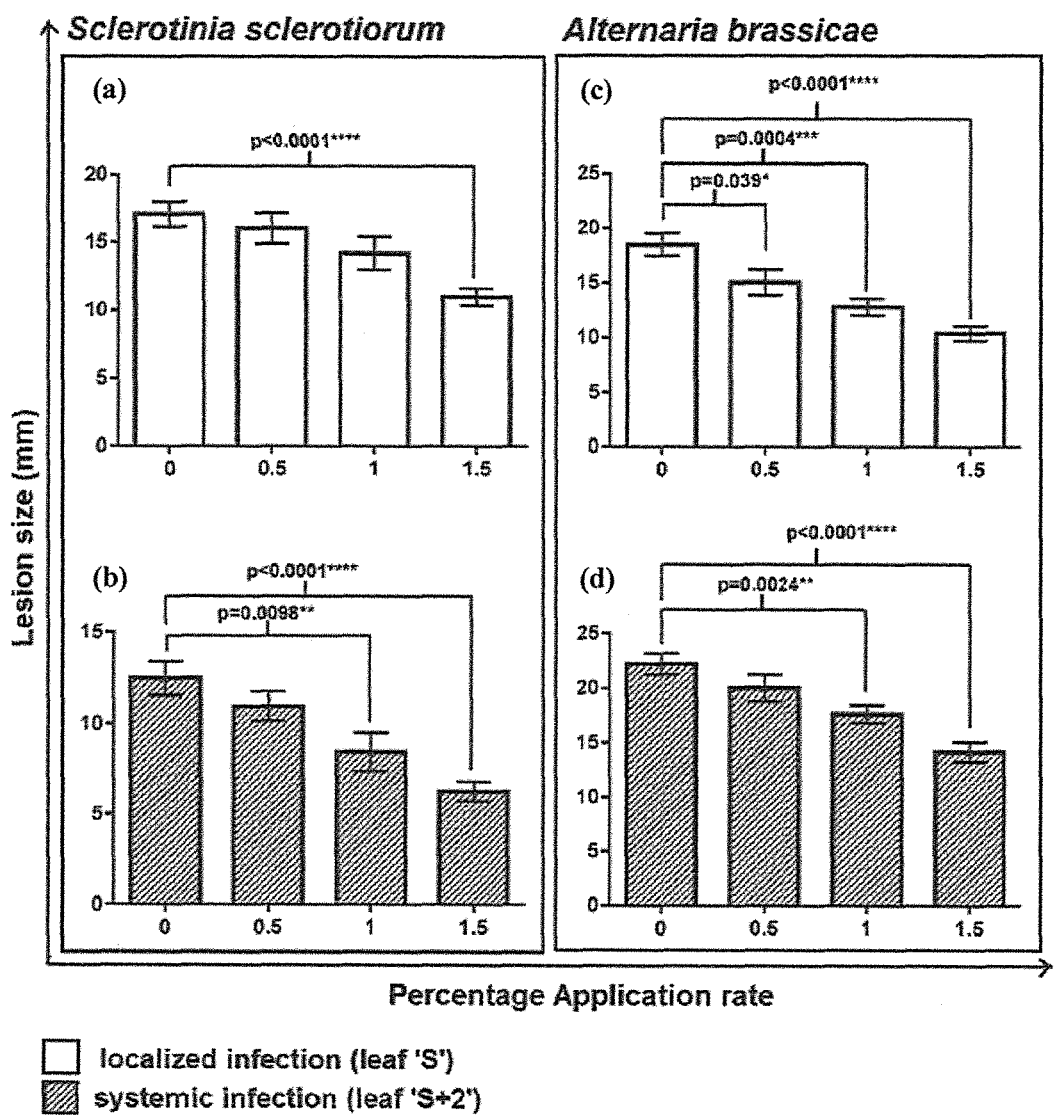
FIGS. 3 A-D are graphs demonstrating the efficacy of Composition 2 in reducing localised and systemically induced fungal lesions in oilseed rape plants grown under glasshouse conditions.

Further analysis of the efficacy of Composition 2 demonstrates an effect in reducing localised and systemically induced necrotrophic fungal lesions in oilseed rape plants (n=10 per treatment) grown under glasshouse conditions (minimum temperature: 12° C.). Localised *Sclerotinia sclerotiorum* lesion diameter was reduced by over 35% at the highest application rate (1.5%; p-value <0.0001****; FIG. 3 (*a*), while lesion size was reduced by over 43% in systemically infected leaves at the same rate of application (S+2, systemic infection; p-value <0.0001****; (b). Similarly, localised *Alternaria brassicae* lesions were reduced by over 49% (p-value <0.0001****; FIG. 3 (*c*) with a greater than 36% reduction observed in systemically infected leaves (S+2); p-value <0.0001****; FIG. 3(*d*). This trial demonstrates that Composition 2 is effective in reducing the size of fungal lesions induced by necrotrophic fungal pathogens *Alternaria brassicae* and *Sclerotinia sclerotiorum*. In particular, Composition 2 treatment achieves reductions in size of lesions arising from both localised and systemic infection. This systemic reduction is most notable in the case of *Sclerotinia sclerotiorum* infections, in which a greater reduction in lesion size is achieved on leaves S+2 (systemic infection), compared to Leaf 'S' (local infection). These effects are to likely apply to other fungal pathogens including biotrophic species.

TABLE 1

Effect of compositions on total yield and marketable yield in 2008.

| | Average yield per plot (11.2 m²) | | | | | | | | | | Yield increase Vs. controls (%) | | | |
|---|---|---|---|---|---|---|---|---|---|---|---|---|---|---|
| | Tuber Numbers | | | | | Tuber Weights (g) | | | | | | | | |
| | | | | | | | | | | | Total | | Marketable | |
| Treatment | >65 mm | 45 mm- 65 mm | <45 mm | tuber No. | Market- able yield | >65 mm | 45 mm- 65 mm | <45 mm | Total yield | Market- able yield | Tuber no. | Weight | Tuber no. | Weight |
| Control | 33 | 60 | 32 | 125 | 93 | 9961 | 8094 | 1279 | 19334 | 18055 | n/a | n/a | n/a | n/a |
| Nematicide (Vydate) | 34 | 62 | 26 | 123 | 96 | 9394 | 9386 | 1249 | 20029 | 18780 | -2% | 4% | 3% | 4% |
| Composition 1 | 33 | 80 | 28 | 141 | 113 | 9837 | 11253* | 1353 | 22444* | 21091* | 13% | 16%* | 22% | 17%* |
| Composition 2A | 30 | 83* | 34 | 147 | 113 | 8598 | 11438* | 1452 | 21488 | 20036 | 18% | 11% | 22% | 11% |

Potato yields achieved in 2008 on treatment with Composition 1, Composition 2A and Nematicide (Vydate) are described in the table above and classified according to marketable grade. Asterisks denote statistically significant increases in yield and marketable grade over untreated controls.
Level of statistical significance denoted as follows:
*P ≤ 0.05.

TABLE 2

Effect of Composition 1 on total yield yield in 2009

|  | Average yield per drill (2.59 m²) | |
|---|---|---|
| Treatment | Total Yield (Weight, g) | Yield increase Vs. controls (%) |
| Control | 3801.44 | n/a |
| Nematicide (Vydate) | 12817.38**** | +131.8%**** |
| Composition 1 | 5527.81# | +45%# |

Total potato yields achieved in 2009 on treatment with Composition1 and Nematicide (Vydate).
Asterisks denote statistically significant increases in yield over untreated controls.
Level of statistical significance denoted as follows: #P = 0.09-0.05, ****P ≤ 0.0001.

TABLE 3

Effect of compositions on total yield and marketable yield in 2011.

| | Average yield per drill (2.59 m²) | | | | | | | |
|---|---|---|---|---|---|---|---|---|
| | Tuber Numbers | | | | | Tuber Weights (g) | | |
| Treatment | >65 mm | 45 mm-65 mm | <45 mm | Total tuber No. | Marketable yield | >65 mm | 45 mm-65 mm | <45 mm |
| Control | 2 | 33 | 35 | 69.8 | 35 | 488 | 4860 | 1427 |
| Nematicide (Vydate) | 8* | 48 | 36 | 91.5 | 56** | 2216* | 7125* | 1215 |
| Composition 1 | 2 | 45 | 32 | 78.3 | 47* | 571 | 5842 | 1252 |
| Composition 2B | 7 | 42 | 29 | 77.5 | 49* | 1804 | 6084 | 1397 |

| | Average yield per drill (2.59 m²) | | Yield increase Vs. controls (%) | | | |
|---|---|---|---|---|---|---|
| | Tuber Weights (g) | | Total | | Marketable | |
| Treatment | Total yield | Marketable yield | Tuber no. | Weight | Tuber no. | Weight |
| Control | 6775 | 5349 | n/a | n/a | n/a | n/a |
| Nematicide (Vydate) | 10556*** | 9342*** | 31% | 56%*** | 61%** | 75%**** |
| Composition 1 | 7664 | 6412 | 12% | 13% | 34%* | 20% |
| Composition 2B | 9284* | 7888** | 11% | 37%* | 40%* | 47%** |

Potato yields achieved in 2011 on treatment with Composition1, Composition 2B and Nematicide (Vydate) are described in the table above and classified according to marketable grade. Asterisks denote statistically significant increases in yield and marketable grade over untreated controls.
Levels of statistical significance denoted as follows:
*P ≤ 0.05,
**P ≤ 0.01,
***P ≤ 0.001,
****P ≤ 0.0001.

TABLE 4

Effect of compositions on total yield and marketable yield in 2012.

| | Average yield per drill (2.59 m²) | | | | | | | | | | Yield increase Vs. controls (%) | | | |
|---|---|---|---|---|---|---|---|---|---|---|---|---|---|---|
| | Tuber Numbers | | | | | Tuber Weights (g) | | | | | Total | | Marketable | |
| Treatment | >55 mm | 35 mm-55 mm | <35 mm | Total tuber No. | Marketable yield | >55 mm | 35 mm-55 mm | <35 mm | Total yield | Marketable yield | Tuber no. | Weight | Tuber no. | Weight |
| Control | 25 | 42 | 13 | 79 | 66 | 2780 | 1874 | 274 | 4929 | 4654 | n/a | n/a | n/a | n/a |
| Nematicide (Vydate) | 34* | 35 | 8 | 77 | 69 | 4551** | 1749 | 179* | 6479** | 6300** | -2% | 31%** | 5% | 35%** |
| Composition 1 | 24 | 47 | 19** | 90 | 71 | 2760 | 2208 | 383* | 5351 | 4968 | 14% | 9% | 8% | 7% |

TABLE 4-continued

Effect of compositions on total yield and marketable yield in 2012.

| | Average yield per drill (2.59 m$^2$) | | | | | | | | | Yield increase Vs. controls (%) | | | |
|---|---|---|---|---|---|---|---|---|---|---|---|---|---|
| | Tuber Numbers | | | | | Tuber Weights (g) | | | | | | | |
| | | | | Total | Market- | | | | | Market- | Total | | Marketable | |
| Treatment | >55 mm | 35 mm-55 mm | <35 mm | tuber No. | able yield | >55 mm | 35 mm-55 mm | <35 mm | Total yield | able yield | Tuber no. | Weight | Tuber no. | Weight |
| Composition 2C | 35** | 38 | 12 | 85 | 74 | 4571** | 1878 | 246 | 6695** | 6449** | 8% | 36%** | 12% | 39%** |
| Seed treatment | 23 | 47 | 14 | 84 | 70 | 2627 | 2232 | 299 | 5158 | 4695 | 6% | 5% | 6% | 1% |

Potato yields achieved in 2012 on treatment with Composition1, Composition 2C and Nematicide (Vydate) are described in the table above and classified according to marketable grade.
Asterisks denote statistically significant increases in yield and marketable grade over untreated controls.
Levels of statistical significance denoted as follows:
*P ≤ 0.05,
**P ≤ 0.01.

TABLE 5

Effect of compositions on multiplication rate, Pf/Pi, of PCN.

| Treatment | Multiplication rate (Pf/Pi) | Significance |
|---|---|---|
| Fallow | 0.75 | a |
| Control (no Treatment) | 17.28 | b |
| Full rate Nematicide (Vydate) | 0.62 | a |
| Composition 1 | 7.04 | b |
| Composition 2B | 18.23 | b |

Within columns means sharing the same letter are not significantly different (significance at the p < 0.05 level).
This trial was undertaken in 2011.

Example 2

Aims: To examine the effects of Composition 1 and fucoidan on plant root growth in nematode infested growth media.

Materials and Methods:

The effects of Composition 1 and fucoidan on Creeping bentgrass and Perennial ryegrass root growth were examined in the laboratory setting in the presence or absence of plant parasitic nematodes in 2010. Seeds were pre-soaked in test materials for 16 hours each and left to germinate on wet USGA sand at 16° C. Roots were analysed using WinRHIZO image analysis system, following a 7 day period to assess mean root length following applications (n=10 seedlings per treatment). Experiments were also undertaken to assess the efficacy of Composition 1 and fucoidan in enhancing root length in the presence or absence of plant pathogenic nematodes. Seedlings (×7 replication) were established in sand columns containing USGA specification sand and sprayed on a weekly basis with either Composition 1 or fucoidan. Composition 1 was applied according to the same bioactive ratio as in 2008, but at a substantially increased rate corresponding to 1460 g of bioactives applied per hectare. Fucoidan was applied at a rate equivalent to 600 g/Ha. Root knot nematodes of the species *Meloidogyne minor* were inoculated around the roots in week 1, as second stage juveniles. Roots were analysed using WinRHIZO image analysis system following a 25 days period.

Results:

While Composition 1 had no effect on early root growth of either species of grass, a significant increase in mean root length of perennial ryegrass was achieved by soaking seeds in fucoidan versus untreated controls (48.9 mm versus 43.0 mm, p-value <0.05*, Table 6). In the absence of *Meloidogyne minor* infestation, Composition 1 was associated with a significant increase in Perennial ryegrass seedling root growth compared to untreated controls (79.6 mm versus 69.4 mm, p-value<0.05*, Table 7). A substantial increase was observed in the presence of nematodes (97.4 mm versus 42.3 mm, p-value<0.05), suggesting enhanced efficacy of Composition 1 in the presence of nematodes. Treatment with fucoidan was highly effective in increasing root growth in the absence of nematodes, thus suggesting a high level of efficacy for fucoidan in enhancing perennial ryegrass root growth in non-nematode infested growth media. In the presence of nematodes, efficacy was also highly effective.

Significant increases in root growth were also observed on treating Creeping bentgrass with Composition 1 and fucoidan. In the absence of *Meloidogyne minor* infestation, Composition 1 resulted in a significant increase in root growth compared to the control (22.8 mm versus 17.4 mm, p-value<0.05*, Table 7). Likewise, a significant increase in root-length on application of Composition 1 was achieved in the presence of nematodes as compared with untreated controls (18.7 mm versus 12.4 mm, p-value<0.05*). Treatment with fucoidan yielded comparable results.

TABLE 6

Effect of pre-soaking seeds with Composition 1 and fucoidan on early root growth.

| | Mean Root length (mm) | |
|---|---|---|
| Treatment | Perennial ryegrass (n = 10) | Creeping bentgrass (n = 10) |
| Control | 43.0 [a] | 37.9 [a] |
| Composition 1 | 38.1 [a] | 37.7 [a] |
| Fucoidan | 48.9 [b] | 39.1 [a] |

Within columns means sharing the same letter are not significantly different (significance at the p < 0.05 level).

TABLE 7

Effects of Composition 1 and fucoidan on Perennial ryegrass and Creeping bentgrass mean root length (mm) in the presence and absence of plant pathogenic nemtodes.

| Perennial ryegrass (n = 7) | | | Creeping bentgrass (n = 7) | | |
|---|---|---|---|---|---|
| Application | −Mm | +Mm | Application | −Mm | +Mm |
| Control | 69.4$^a$ | 42.3$^a$ | Control | 17.4$^a$ | 12.4$^a$ |
| Composition 1 | 79.6$^b$ | 97.4$^b$ | Composition 1 | 22.8$^b$ | 18.7$^b$ |
| Fucoidan | 129.2$^c$ | 102.2$^b$ | Fucoidan | 27.1$^b$ | 20.2$^b$ |

Within columns means sharing the same letter are not significantly different (significance at the p < 0.05 level).
'+Mm', denotes inoculation with *Meloidogyne* minor;
'−Mm', denotes conditions where inoculation with *Meloidogyne* minor did not take place.

Discussion

These experiments demonstrate that Composition 1 and a purified component thereof (fucoidan) significantly increases root growth of creeping bentgrass and perennial ryegrass in growth media infested with root knot nematodes, of the species *Meloidogyne minor*. Moreover, Composition 1 was shown to be as effective as fucoidan in the presence of nematodes, in spite of the composition containing lower levels of this bioactive. This suggests that the significant effects imparted by Composition 1 may be attributed to the presence of additional bioactives in the product which may be acting in synergy with fucoidan to stimulate plant growth in the presence of nematodes (laminarin and/or mannitol). Moreover, these findings indicate that the efficacy of such compositions may be increased when applied at rates which ensure high levels of bioactives are applied per hectare. This hypothesis was tested in field trials in 2011, 2012 (see Example 1) and in 2013 (Experiment 3).

Composition 1 was less effective than fucoidan in the absence of nematodes, with fucoidan also having significant effects in both nematode infested and nematode-free media alike (Perennial ryegrass experiment). This indicates that fucoidan is highly effective in both a stressed and non-stressed environments. The efficacy of Composition 1 which contains lower levels of fucoidan may be enhanced in the presence of additional molecules (e.g. laminarin, mannitol) which act synergistically to obtain greater effects in nematode infested media. In addition, fucoidan was also effective as a treatment to Perennial ryegrass at pre-germination stages, with Composition 1 only effective in enhancing root growth when applied to established seedlings. Thus, while fucoidan represents an effective growth promoting composition when applied at the seed treatment stage, Composition 1 is as effective as fucoidan as a treatment once seedlings are established. Again, this points to synergistic effects between bioactives such as laminarin/mannitol and fucoidan in Composition 1, effects which may become more apparent once seeds are established but less so before germination.

In conclusion, treatment with Composition 1 and fucoidan are found to significantly increase creeping bentgrass and perennial ryegrass root growth in the presence of nematode infestation. From an economical point of view, Composition 1 would provide greater return on investment to growers due to the lower costs associated with it's production, while fucoidan would be less viable given the costs associated with purification. The significant effects observed with Composition 1 suggests a synergistic mode of action between fucoidan and other bioactives contained in the composition, such as laminarin and/or mannitol. Moreover, these findings indicate that composition efficacy is enhanced by ensuring high levels of bioactives are applied per hectare, an effect confirmed in field trials in 2011 and 2012 (see Example 1). The hypothesis that interactions between bioactives are potentially synergistic in their effects, was investigated in a field trial in 2013 (Example 3).

Example 3

Aims: To determine the efficacy of glucan-alone, mannitol-alone, glucan+fucan, glucan+mannitol and fucan+mannitol in enhancing yield of potatoes grown in soil infested with plant-pathogenic nematodes, as compared with DuPont™ Vydate® (oxamyl).

Materials and Methods:

Differences in efficacy achieved with Composition 1 and Composition 2 in field trials between 2008-2012 pointed to a differential effect of bioactive levels within the two compositions (Example 1). Laboratory trials on grass species grown in the presence of *Meloidogyne minor* identified fucan (fucoidan) as one of the bioactives responsible for enhancing growth (Example 2). Despite lower levels of fucoidan, Composition 1 also achieved equivalent increases in root growth in the same trial as compared with the purified fucoidan. This suggested a synergistic effect of fucoidan with other bioactives within the composition, such as glucan and/or mannitol. A field trial was undertaken in 2013 to further determine which bioactives or combinations of bioactives are responsible for conferring enhancements in total and marketable yield in nematode infested growth media. As in previous trials, the forms of glucan and fucan used were laminarin and fucoidan respectively.

Bioactives were isolated and stock solutions prepared to contain glucan alone, mannitol alone, glucan+mannitol, fucan+mannitol and glucan+fucan. The efficacy of the bioactive fractions were assessed in plots known to be infested with *Globodera pallida*. Treatments were fully randomized with plots of approximately 16 m$^2$ in area and 6 drills wide. Twelve tubers were planted per drill. One metre spacing was placed between blocks with two drills fallow between treatments. The dimensions of the drills were 0.7 meters wide and 3.7 meters in length. The cultivar Navan, (*Solanum tuberosum* L. cv. Navan) was planted and compositions applied by foliar spray at 50% post-emergence and at approximately seven day intervals thereafter. Foliar spray ceased once senescence was noticed. For each of the 5 treatments, a total of 621 g of bioactives was applied per Ha. A nematicidal treatment, Vydate, was applied at full rate as a separate treatment. Standard compound fertilizers and fungicides were applied at recommended rates and intervals. The crop was harvested in November. Total harvest weight and marketable yield (>35 mm category) was measured, with comparisons between bioactive treatments and nematicide made by means of One-Way ANOVA.

Results:

Glucan-Alone

Total yield in the glucan-alone treatment was statistically indistinguishable to Vydate (10524 g vs. 11337 g, p-value=0.21). Marketable yield with glucan-alone was also statistically indistinguishable to Vydate (10218 g vs. 11009 g, p-value=0.22). This demonstrates that yields achieved on treatment with glucan-alone are comparable to those achieved with Vydate.

Mannitol-Alone

Total yield in the mannitol-alone treatment was significantly lower than that achieved with Vydate (9652 vs. 11337 g, p-value=0.009**). This was also observed at the level of total marketable yield (9324 vs. 11009 g, p-value=0.01*). This demonstrates that mannitol-alone does not achieve yields comparable to Vydate.

Glucan+Mannitol

Treatment with glucan+mannitol was associated with an almost 6% increase in total yield compared to that achieved with full rate Vydate (12028 g vs. 11337 g, p-value=0.28). Similarly, marketable yield was 6.7% higher for the glucan+mannitol treatment compared to Vydate (11748 g vs. 11009 g, p-value=0.25). This demonstrates that yields achieved on treatment with glucan+mannitol are comparable to those achieved with Vydate.

Mannitol+Fucan

Treatment with mannitol+fucan was associated with a total yield statistically indistinguishable to Vydate (11549 g vs. 11337 g, p-value=0.74). Marketable yield was also marginally higher and statistically indistinguishable from Vydate (11352 g vs. 11009, p-value=0.59). This demonstrates that yields achieved on treatment with mannitol+fucan are comparable to those achieved with Vydate.

Glucan+Fucan

Total yield achieved with glucan+fucan treatment was statistically indistinguishable from that achieved with Vydate (10650 g vs. 11337, p-value=0.29) and similar to that achieved with glucan alone (10524 g). Likewise, marketable yield in both treatments were also statistically indistinguishable (10433 g vs. 11009 g, p-value=0.37). This demonstrates that yields achieved on treatment with glucan+fucan are comparable to those achieved with Vydate.

Discussion

The aim of this trial was to compare yields achieved with glucan-alone, mannitol-alone, glucan+mannitol, fucan+mannitol and glucan+fucan with those achieved with a commercial nematicide, Vydate. In most cases, yields were found to be comparable and statistically indistinguishable to Vydate. Yield with mannitol-alone, however, was significantly lower than Vydate. Glucan-alone in contrast, provided a yield comparable to Vydate.

In contrast to their effects as single bioactive fractions, the effectiveness of glucan-alone and mannitol-alone were substantially enhanced by the presence of additional molecules. Of note, glucan+mannitol and mannitol+fucan treatments were associated with the highest marketable yields in the entire trial, and in both cases reached levels marginally higher than Vydate, albeit not significantly so. This points to a striking level of synergy between the bioactives. While mannitol-alone did not provide yields comparable to nematicide, the yield achieved with mannitol in the presence of fucoidan was comparable to both glucan+mannitol and Vydate. In addition, the glucan+fucan treatment was also associated with yields statistically indistinguishable to Vydate and marginally higher than glucan-alone.

This trial demonstrates the efficacy of individual and synergistic combinations of laminarin, laminarin & mannitol, laminarin & fucoidan and fucoidan and mannitol. Optimal application rates of individual bioactives and their synergistic combinations are as specified in Example 1. The rate of ≥400 g/ha refers to either the sum total of all three bioactives together, the sum total of dual synergistic combinations of the bioactives or the amount applied per hectare when applying the bioactives as individual, singular applications.

TABLE 8

Effect of bioactives on total yield and marketable yield in 2013.

| | Average yield per drill (2.59 m$^2$) | |
|---|---|---|
| Treatment | Total Weight (g) | Marketable weight (g) |
| Full rate Nematicide | 11337 | 11009 |
| Glucan-alone | 10524 | 10218 |
| Mannitol-alone | 9652** | 9324* |
| Glucan + Mannitol | 12028 | 11748 |
| Mannitol + Fucan | 11549 | 11352 |
| Glucan + Fucan | 10650 | 10433 |

Potato yields achieved in 2013 on treatment with glucan-alone, mannitol-alone, glucan + fucan, glucan + mannitol, fucan + mannitol and nematicide (Vydate) are described in the table above.
Asterisks denote statistically significant differences in yield versus full rate of nematicide. Levels of statistical significance are denoted as follows: *P ≤ 0.05, **P ≤ 0.01.

CONCLUSIONS

In conclusion, this trial demonstrates that glucan-alone, glucan+mannitol, mannitol+fucan and fucan+glucan, but not mannitol-alone, achieve yields to levels which are statistically indistinguishable to Vydate. Furthermore this study demonstrates that the efficacy of these bioactives are enhanced when present in synergistic combinations of glucan+mannitol, fucan+mannitol and glucan+fucan, each of which increased marketable yield to levels statistically equivalent to nematicide.

Modification and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described which may be varied in construction and detail.

REFERENCES

Anger W K (2003) Neurobehavioural tests and systems to assess neurotoxic exposures in the workplace and community. Occup Environ Med 60(7): 531-538, 474

Ara, J., V. Sultana, R. Qasim, S. Ehteshamul-Haque and V. U. Ahmad 2005. Biological activity of *Spatoglossum asperum*: a brown alga. Phytother. Res., 19: 618-623.

Bardgett R D, Denton C S, Cook R (1999) Below-ground herbivory promotes soil nutrient transfer and root growth in grassland. Ecol Lett 2:357-360

Bardin P G, van Eeden S F, Moolman J A et al (1994) Organophosphate and carbamate poisoning. Arch Intern Med 154(13):1433-1441

Bell N L, L T Aalders, N R Cox, C A Cameron. Non-target effects of a carbamate and the proteins avidin and aprotinin on in vitro development of a bacterial feeding nematode. Soil Biology and Biochemistry. Volume 38, Issue 9, September 2006, Pages 2816-2822

Bird D M, Kaloshian I. Are roots special? Nematodes have their say. Physiological and Molecular Plant Pathology. 2003; 62:115-123.

Blondin C, Chaubet F, Nardella A, Sinquin C, Jozefonvicz J. Relationships between chemical characteristics and anticomplementary activity of fucans. Biomaterials. 1996 March; 17(6):597-603.

Bocquene, G., Franco, A., 2005. Pesticide contamination of the coastline of Martinique. Marine Pollution Bulletin 51, 612-619.

Boran, M., Altinok, I., Capkin, E., Karacam, H. and Bicer, V. 2007. Acute toxicity of carbaryl, methiocarb, and carbosulfan to the rainbow trout Oncorhynchus mykiss and guppy (*Poecilia reticulata*). Turk J. Vet. Anim. Sci., 31 (1): 39-45.

Bowman, B T (1988). Mobility and persistence of metachlor and aldicarb in field lysimeters. Journal of Environmental Quality 17:689-694.

Bushway R. J. (1981) High-performance liquid chromatographic determination of carbaryl and 1-naphtol at residue levels in various water sources by direct injection and trace enrichment. J. Chromatogr. 211, 135-143.

Bridge, J. and J. L. Starr (2007). Plant nematodes of agricultural importance, a colour handbook. Manson Publishing Ltd, London (U K).

Bushway R. J., Hurst H. L., Perkins L. B., Tian L., Guiberteau Cabanillas C., Young B. E. S., Ferguson B. S. and Jennings H. S. (1992) Atrazine, Alachlor and Carbofuran contamination of well water in Central Maine. Bull. Environ. Contam. Toxicol. 49, 1-9.

Carneiro, R. G., Mazzafera, P., Ferra, L. C. C. B., Muraoka, T., and Trivelin, P. C. O. 2002. Uptake and translocation of nitrogen, phosphorus and calcium in soybean infected with *Meloidogyne incognita* and *M. javanica*. Fitopatol. Bras. 27(2): 141-150.

Castagnone-Sereno, P. 2006. Genetic variability and adaptive evolution in parthenogenetic root-knot nematodes. Heredity 96:282-289.

Cheng X Y, Tian X L, Wang Y S, Lin R M, Mao Z C, Chen N & Xie B Y (2013) Metagenomic analysis of the pinewood nematode microbiome reveals a symbiotic relationship critical for xenobiotics egradation. Scientific Reports 3, 1869.

Chinnasri B, Sipes B S, Schmitt D P. Effects of Inducers of Systemic Acquired Resistance on Reproduction of *Meloidogyne javanica* and *Rotylenchulus reniformis* in Pineapple. J Nematol. 2006 September; 38(3):319-25.

Chiron S. and Barceló D. (1993) Determination of pesticides in drinking water by on-line solid-phase disk extraction followed by various liquid chromatographic systems. J. Chromatogr. 645, 125-134.

Chiron S., Dupas S., Scribe P. and Barceló D. (1994) Application of on-line solid-phase extraction followed by liquid chromatography thermospray mass spectrometry to the determination of pesticides in environmental waters. J. Chromatogr. A. 665, 295-305.

Chitwood D J, 2003. "Nematicides," in Encyclopedia of Agrochemicals (3), pp. 1104-1115, John Wiley & Sons, New York, N.Y.

Chojnacka K, Saeid A, Witkowska Z and Tuhy L. Biologically Active Compounds in Seaweed Extracts—the Prospects for the Application. The Open Conference Proceedings Journal, 2012, 3, (Suppl 1-M4) 20-28

Cone, M (2010). Toxic Pesticide Banned after Decades of Use: Scientific American. Scientific American, 18 August Cook R and Noel G R (2002). Cyst Nematodes: *Globodera* and *Heterodera* Species. pages 71-105. In Plant Resistance to Parasitic Nematodes eds. J. L. Starr, R. Cook and J. Bridge. CAB International Cowgill, S. E., Bardgett, R. D., Kiezebrink, D. T., and Atkinson, H. J. 2002. The effect of transgenic nematode resistance on non-target organisms in the potato rhizosphere. Journal of Applied Ecology 39:915-923.

Crouch I J and Van Staden J. Effect of seaweed concentrate from *Ecklonia maxima* (Osbeck) Papenfuss on *Meloidogyne incognita* infestation on tomato. Journal of Applied Phycology 5: 37-43, 1993A.

Crouch I. J. and J. van Staden. Evidence for the presence of plant growth regulators in commercial seaweed products. Plant Growth Regulation 13: 21-29, 1993B.

Cui, W., Wood, P. J., Blackwell, B., & Niliforuk, J. (2000). Carbohydrate Polymers, 41(3), 249-258.

de Deyn G B, Raaijmakers C E, van der Putten W H. 2004. Plant community development is affected by nutrients and soil biota. J. Ecol. 92:824-34

De Waele D, McDonald A H, De Waele E. 1988. Influence of seaweed concentrate on the reproduction of *Pratylenchus zeae* (Nematoda) on maize. Nematologica. 34:71-77

Dikshith T. S. S., Kumar S. N., Raizada R. P., Srivastava M. K. and Ray P. K. (1990) Residues of 1-naphtol in soil and water samples in and around Bhopal, India. Bull. Environ. Contam. Toxicol. 44, 87-91.

DuPont™ Vydate® insecticide/nematicide, Technical Bulletin. Protect your crops against damage from insects, mites and nematodes. Source: http://www2.dupont.com/Production_Agriculture/en_US/assets/downloads/pdfs/H-95402.pdf, accessed: 11_01_2013

Dursun A and Ekinci M (2012). Effects of different priming treatments and priming durations on germination percentage of parsley (*Petroselinum crispum* L.) seeds. Agricultural Sciences. Vol. 1, No. 1, 17-23

ECPRF Expert Committee on Pesticide Residues in Food (2012). Pesticide Residues Monitoring Programme for Quarter 4 2011 [Online] Available at http://www.pesticides.gov.uk/Resources/CRD/PRiF/Q4_2011_report.pdf (Accessed Nov. 1, 2013).

Ellenby, C. 1954. Environmental determination of the sex ratio of a plant-parasitic nematode. Nature 174:1016.

EPA (2010). Agreement to Terminate All Uses of Aldicarb. Source: U. S. Environmental Protection Agency's Office of Pesticide Programs, EPA Pesticide Program. http://www.epa.gov/oppsrrdl/REDs/factsheets/aldicarb_f-s.html.

EPA (2013) What is a pesticide? Source: http://www.epa.gov/pesticides/about/index.htm [accessed Jan. 10, 2013]

European Commission (EU), "Directive 2009/128/EC of the European Parliament and of the Council of 21 Oct. 2009 Establishing a Framework for Community Action to Achieve the Sustainable Use of Pesticides,"

European Commission (EU), "Directive 2009/128/EC of the European Parliament and of the Council of 21 Oct. 2009 Establishing a Framework for Community Action to Achieve the Sustainable Use of Pesticides,"

EU Regulation REGULATION (EC) No 178/2002 OF THE EUROPEAN PARLIAMENT AND OF THE COUNCIL of 28 Jan. 2002. Laying down the general principles and requirements of food law, establishing the European Food Safety Authorityand laying down procedures in matters of food safety.

FAO/WHO, (2002), Pesticide residues in food. Report of the Joint Meeting of the FAO Panel of Experts on Pesticide Residues in Food and the Environment and the WHO Core Assessment Group on Pesticide Residues Rome, Italy, 16-25, pages 198-213.

Farahat T M, Abdelrasoul G M, Amr M M et al (2003) Neurobehavioral effects among workers occupationally exposed to organophosphate pesticides. Occup Environ Med 60:279-286

Featonby-Smith B C, van Staden J. 1983. The effect of seaweed concentrate on the growth of tomato plants in nematode infested soil. Sci. Hortic. 20:137-46

Ferris H (2001). NEMAPLEX: The Nematode-Plant Expert Information System. Web: http://plpnemweb.ucdavis.edu/nemaplex/Nemaplex.htm [Access date: 18 Mar. 2014].

Garcia de Llasera M. P., Bernal-Gonzalez, M.: Presence of carbamate pesticides in environmental waters from the northwest of Mexico: Determination by liquid chromatography. Water Res., 2001; 35: 1933-1940

Garcia-M., R., and J. R. Rich. 1983. Efficacy of selected fumigant and nonfumigant nematicides to control *Meloidogyne javanica* in Florida tobacco. Nematr6pica 13:125-134.

Gowen S R, 1992. Chemical control of nematodes: efficiency and side-effects. in Plant Nematode Problems and their Control in the Near East Region (FAO Plant Production and Protection Paper—144), 1992.

Grue, C. E., Fleming, W. J., Busby, D. G., Hill, E. F.: Assessing hazards of organophosphate pesticides to wildlife. In: Transactions of the 48th North American Wildlife and Natural Resources Conference. The Wildlife Management Institute, Washington, D C. 1983; 200-220.

Grundler, F., M. Betka, and U. Wyss. 1991. Influence of changes in the nurse cell system (syncytium) on sex determination and development of the cyst nematode *Heterodera schachtii*: Total amounts of proteins and amino acids. Phytopathology 81:70-74.

Hamamouch N, Li C, Hewezi T, Baum T J, Mitchum M G, Hussey R S, Vodkin L O, Davis E L. The interaction of the novel 30C02 cyst nematode effector protein with a plant β-1,3-endoglucanase may suppress host defence to promote parasitism J. Exp. Bot. (2012) 63(10): 3683-3695

Hussey, R. S. (1989). Disease-inducing secretions of plant-parasitic nematodes. Annu. Rev. Phytopathol. 27, 123-141.

Hussey R S and G. J. W. Janssen. 2002. Root-knot nematodes: *Meloidogyne* Species. pages 43-70 In Plant Resistance to Parasitic Nematodes eds. J. L. Starr, R. Cook and J. Bridge. CAB International Ingham R E, Trofymow J A, Ingham E R, Coleman D C. 1985. Interactions of bacteria, fungi, and their nematode grazers: effects on nutrient cycling and plant growth. Ecol. Monogr. 55:119-40

Ibekwe A M. (2004). Effects of fumigants on non-target organisms in soils. Adv Agron 83: 1-35.

Jenkins T, Blunden G, Wu Y, Hankins S D, Gabrielsen B O. 1998. Are the reductions in nematode attack on plants treated with seaweed extracts the result of stimulation of the formaldehyde cycle? Acta Biol. Hung. 49:421-27

Kikuchi T, Shibuya H, Jones J T (2005) Molecular and biochemical characterization of an endo-beta-1,3-glucanase from the pinewood nematode *Bursaphelenchus xylophilus* acquired by horizontal gene transfer from bacteria. Biochem J 389: 117-125.

Kimpinski, J., Martin, R. A., and Sturz, A. V. 2005. Nematicides increase grain yields in spring wheat cultivars and suppress plant-parasitic and bacterial-feeding nematodes. Journal of Nematology 37:473-476.

Kirkpatrick, T. L., Oosterhuis, D. M. & Wullschleger, S. D. Interaction of *Meloidogyne incognita* and water stress in two cotton cultivars. Journal of Nematology 23:462-467.1991.

Klarzynski O., Plesse B., Joubert J. M., Yvin J. C., Kopp M. Kroareg B., and Fritig B. (2000) Linear β-1,3 glucans are elicitors of defence responses in Tobacco. Plant Physiology Vol. 124, pp 1027-1038

LaMondia, J. A., 2006. Management of lesion nematodes and potato early dying with rotation crops. Journal of Nematol. 38, 442-448.

Leonard S. G., Sweeney T., Bahar B., Lynch B. P. and O'Doherty J. V. Effect of dietary seaweed extracts and fish oil supplementation in sows on performance, intestinal microflora, intestinal morphology, volatile fatty acid concentrations and immune status of weaned pigs. British Journal of Nutrition. 2011A, 105: 549-560.

Leonard S G, Sweeney T, Bahar B, Lynch B P, O'Doherty J V. Effects of dietary seaweed extract supplementation in sows and post-weaned pigs on performance, intestinal morphology, intestinal microflora and immune status. British Journal of Nutrition. 2011B September; 106(5): 688-99.

Li, Y., J. Gupta and A. K. Siyumbano, 1995. Effect of methanol on soybean photosynthesis and chlorophyll. J. Plant Nutr., 18: 1875-1880.

Loison M., 2012. Alternative control of nematodes makes its first steps. New Ag International, Issue 3, September/October, page 26-30.

London L, Nell V, Thompson M L et al (1998) Effects of long-term organophosphate exposures on neurological symptoms, vibration sense and tremor among South African farm workers. Scand J Work Environ Health 24(1): 18-29

MacGregor, A. W. a. B., & Rattan, S. (1993). Barley chemistry and technology. St. Paul, USA: American Association of Cereal Chemists Inc.

Mackenzie Ross S J, Brewin C R, Curran H V et al (2010) Neuropsychological and psychiatric functioning in sheep farmers exposed to low levels of organophosphate pesticides. Neurotoxicol Teratol 32:452-459

Magnelli P, Cipollo J. F. and Abeijon C., Analytical Biochemistry, 301 (2002), 136-150 Mahan, D. C., 1992. Journal of Animal Science 70: 2182-2187.

Martin T J, Turner S J, Fleming C C. Management of the potato cyst nematode (*Globodera pallida*) with bio-fumigants/stimulants. Commun Agric Appl Biol Sci. 2007; 72(3):671-5.

McDonnell, P.; Figat, S.; O'Doherty, J. V. The effect of dietary laminarin and fucoidan in the diet of the weanling piglet on performance, selected fecal microbial populations and volatile fatty acid concentrations. Animal 2010, 4, 579-585.

Means, T. K (2010). Fungal pathogen recognition by scavenger receptors in nematodes and mammals. Virulence 1, 37-41.

Neher D A, Ecology of plant and free-living nematodes in natural and agricultural soil, Annu. Rev. Phytopathol. 48 (2010) 371-394.

Noling, J W (2002). Movement and toxicity of nematicides in the plant root zone. Institute of Food and Agricultural Sciences Fact Sheet ENY-041, University of Florida Department of Entomology and Nematology, Florida Cooperative Extension Service. Online: http://edis.ifas.ufl.edu/pdffiles/NG/NG00200.pdf (accessed Jan. 10, 2013).

Nonomura A M, Benson A A. The path of carbon in photosynthesis: improved crop yields with methanol. Proc Natl Acad Sci USA. 1992 Oct. 15; 89(20):9794-8.

Nordmeyer, D. J. R. Rich, and D. W. Dickson. 1982. Effect of ethoprop, carbofuran, and aldicarb on flue-cured tobacco infected with three species of *Meloidogyne*. Nematropica 12:190-204.

Novak M, Vetvicka V. Glucans as biological response modifiers. Endocr Metab Immune Disord Drug Targets. 2009 March; 9(1):67-75.

Okada, H., Harada, H. & Kadota, I. (2004). Application of diversity indices and ecological indices to evaluate nematode community changes after soil fumigation. Japanese Journal of Nematology 34, 89-98.

O'Malley M A, Fong H, Mehler L et al (2011) Illness Associated with Exposure to Methyl Bromide-Fumigated Produce—California, 2010. MMWR 60:923-926

Pankhurst, C. E., Blair, B. L., Magarey, R. C., Stirling, G. R., and Garside, A. L. 2005. Effects of biocides and rotation breaks on soil organisms associated with the poor early growth of sugarcane in continuous monoculture. Plant & Soil 268:255-269.

Paracer S, Tarjan A C, Hodgson L M. 1987. Effective use of marine algal products in the management of plant-parasitic nematodes. J. Nematol. 19:194-200

Rahi G S, J. R. Rich, and C. H. Hodge (1992). Ethoprop Depletion from Soil as Influenced by Simulated Rainfall. J Nematol. 24(4S): 642-647.

Ramamoorthy V., Viswanathan R., Raguchander T., Prakasam V. and Samiyappan R. Induction of systemic resistance by plant growth promoting rhizobacteria in crop plants against pests and diseases. Crop Protection, Volume 20, Number 1, February 2001, pp. 1-11(11)

Read S, Currie G and Bacic A., Carbohydrate Research, 281 (1996) 187-210 [0212] Riou, D., et al., Anticancer Research, vol. 16, pp. 1213-1218 (1996).

Reeve J R, Schadt C W, Carpenter-Boggs L, Kang S, Zhou J, Reganold J P (2010). Effects of soil type and farm management on soil ecological functional genes and microbial activities. ISME J 4:1099-1107. PMID: 20376100

Reilly, P., J. V. O'Doherty, K. M. Pierce, J. J. Callan, J. T. O'Sullivan and T. Sweeney. The effects of seaweed extract inclusion on gut health and immune status of the weaned pig. Animal 2008, 2 (10):1465-1473.

Rich, J. R., C. Hodge, and J. T. Johnson. 1984. Population development and pathogenicity of *Meloidogyne javanica* on flue-cured tobacco as influenced by ethoprop and D D. Journal of Nematology 16:240-245.

Rivas-San Vicente M, Plasencia J. Salicylic acid beyond defence: its role in plant growth and development. J Exp Bot. 2011 June; 62(10):3321-38. Epub 2011 Feb. 28. Review.

Rohde, W. A., A. W. Johnson, C. C. Dowler, and N. C. Glaze. 1980. Influence of climate and cropping patterns on the efficacy of ethoprop, methyl bromide, and DD-MENCS for control of root-knot nematodes. Journal of Nematology 12:33-39.

Rohlman D S, Anger K W, Lein P J (2011) Correlating neurobehavioral performance with biomarkers of organophosphorus pesticide exposure. NeuroToxicology. 32:268-276

Roldan-Tapia L, Parron T, Sanchez-Santed F (2005) Neuropsychological effects of long-term exposure to organophosphate pesticides. Neurotoxicol Teratol 27(2):259-266

Rosenstock L, Keifer M, Daniell W E et al (1991) Chronic central nervous system effects of acute organophosphate pesticide intoxication. The Pesticide Health Effects Study Group. Lancet 338(8761):223-227

Russo, R. O.; Berlyn, G. P. The use of organic biostimulants to help low input sustainable agriculture. Journal of Sustainable Agriculture 1990 Vol. 1 No. 2 pp. 19-42

Sanchez-Moreno, S., Jiménez, L., Alonso-Prados, J. L., and García-Baudín, J. M. 2010. Nematodes as indicators of fumigant effects on soil food webs in strawberry crops in southern Spain. Ecological Indicators 10:148-156.

Sattler S, Ghadially H, Hofer E (2012). Evolution of the C-Type Lectin-Like Receptor Genes of the DECTIN-1 Cluster in the N K Gene Complex. Scientific World Journal.

Sharma S B (1998) The cyst nematode. Chapman and Hall, London., page 390.

Smith A. G., J. V. O'Doherty, P. Reilly, M. T. Ryan, B. Bahar and T. Sweeney. The effects of laminarin derived from *Laminaria digitata* on measurements of gut health: selected bacterial populations, intestinal fermentation, mucin gene expression and cytokine gene expression in the pig. British Journal of Nutrition. 2011, 105: 669-677.

Smolik, J. D., 1977. Effect of nematicide treatment on growth of range grasses in field and glasshouse studies. In: Marshall, J. K. (Ed.), The Below Ground Ecosystem, vol. 26. Colorado State University range science department series, pp. 257-260.

Stallones L, Beseler C (2002) Pesticide poisoning and depressive symptoms among farm residents. Ann Epidemiol 12(6):389-394

Starks S E, Gerr F, Kamel F, Lynch C F, Alavanja M C, Sandler D P, Hoppin J A (2012). High pesticide exposure events and central nervous system function among pesticide applicators in the Agricultural Health Study. Int Arch Occup Environ Health. 2012 July; 85(5):505-15. doi: 10.1007/s00420-011-0694-8. Epub 2011 Sep. 7.

Steenland K, Jenkins B, Ames R G et al (1994) Chronic neurological sequelae to organophosphate pesticide poisoning. Am J Public Health 84(5):731-736

Stirk, W. A., Van Staden, J. Comparison of cytokinin- and auxin-like activity in some commercially used seaweed extracts. Journal of Applied Phycology. 1997, Volume 8, Issue 6, pp 503-508

Sturz, A. V., and Kimpinski, J. 1999. Effects of fosthiazate and aldicarb on populations of plant-growth-promoting bacteria, root-lesion nematodes and bacteria-feeding nematodes in the root zone of potatoes. Plant Pathology 48:26-32.

Sultana, V., G. N. Baloch, Ambreen, J. Ara, M. R. Tariq and S. Ehteshamul-Haque. 2011. Comparative efficacy of a red alga *Solieria robusta*, chemical fertilizers and pesticides in managing the root diseases and growth of soybean. Pak. J. Bot., 43(1): 1-6.

Tillman P G, Mullinix B G Jr. Comparison of susceptibility of pest *Euschistus servus* and predator *Podisus maculiventris* (Heteroptera: Pentatomidae) to selected insecticides. J Econ Entomol. 2004 June; 97(3):800-6.

Triantaphyllou, A. C., and H. Hirschmann, 1972. Environmentally controlled sex expression in *Meloidodera floridensis*. Journal of Nematology 5:181-185.

Triantaphyllou, A. C. (1973). Environmental sex differentiation of nematodes in relation to pest management. Annu. Rev. Phytopathol. 11, 441-462.

Trudgill, D. L., J. M. Webster, and D. M. Parrott. 1967. The effect of resistant solanaceous plants on the sex ratio of *Heterodera rostochiensis* and the use of the sex ratio to assess the frequency and genetic constitution of pathotypes. Annals of Applied Biology 60:421-428.

UNEP (United Nations Environment Programme), 2005. Division of Technology, et al. Effects of Trade Liberalization on Agriculture in Lebanon: With Special Focus on Products Where Methyl Bromide Is Used. UNEP, page 22.

Vandekerckhove T T M, Willems A, Gillis M, Coomans A (2000). Occurrence of novel verrucomicrobial species, endosymbiotic and associated with parthenogenesis in *Xiphinema americanum*-group species (nematoda, Longidoridae). International Journal of Systematic and Evolutionary Microbiology. 50:2197-2205.

Wada S, Toyota K, Takada A. Effects of the nematicide imicyafos on soil nematode community structure and damage to radish caused by *Pratylenchus penetrans*. J Nematol. 2011 March; 43(1):1-6. PMID: 22791909

Wesseling C, Keifer M, Ahlbom A et al (2002) Long-term neurobehavioral effects of mild poisonings with organophosphate and n-methyl carbamate pesticides among banana workers. Int J Occup Environ Health 8(1):27-34

Whitehead, A. G., Bromilow, R. H., Fraser, J. E. And Nichols, A. J. F. (1985), Control of potato cyst-nematode, *Globodera rostochiensis*, and root-knot nematode, *Meloidogyne incognita*, by organosphosphorus, carbamate, benzimidazole and other compounds. Annals of Applied Biology, 106: 489-498.

Williamson V. M., and Hussey R. S (1996). Nematode pathogenesis and resistance in plants. Plant Cell 8, 1735-1745.

Wolski E, Maldonado S, Daleo G, Andreu A. Cell wall alpha-1,3-glucans from a biocontrol isolate of *Rhizoctonia*: immunocytolocalization and relationship with alpha-glucanase activity from potato sprouts. Mycol Res. 2007 August; 111(Pt 8):976-84. Epub 2007 Jun. 30.

Wu Y, Jenkins T, Blunden G, von Mende N, Hankins S D. 1998. Suppression of fecundity of the root-knot nematode, *Meloidogyne javanica*, in monoxenic cultures of *Arabidopsis thaliana* treated with an alkaline extract of *Ascophyllum nodosum*. J. Appl. Phycol. 10:91-94

Wu Y, Jenkins T, Blunden G, Whapham C, Hankins S D. 1997. The role of betaines in alkaline extracts of *Ascophyllum nodosum* in the reduction of *Meloidogyne javanica* and *M. incognita* infestations of tomato plants. Fundam. Appl. Nematol. 20:99-102

Whapham C A, Jenkins T, Blunden G, Hankins S. 1994. The role of seaweed extracts, *Ascophyllum nodosum*, in the reduction in fecundity of *Meloidogyne javanica*. Fundam. Appl. Nematol. 17: 181-83

Wolski E A, Sara Maldonado, Gustavo R. Daleo, Adriana B. Andreu, A novel α-1,3-glucan elicits plant defense responses in potato and induces protection against *Rhizoctonia solani* AG-3 and *Fusarium solani* f. sp. *eumartii*, Physiological and Molecular Plant Pathology, Volume 69, Issues 1-3, July-September 2006, Pages 93-103, Yeates, G. W., 1985. Effects of 2 nematicides on biological activity in a Typic Haplaquoll at Castlepoint 2. Nematodes. New Zealand Journal of Agricultural Research 28, 141-150.

Yeates, G. W., Prestidge, R. A., 1986. Nematode populations and their effects on herbage production in a volcanic plateau pasture. New Zealand Journal of Agricultural Research 29, 517-523.

Yeates, G. W., Barker, G. M., Pottinger, R. P., 1983. Effects of oxamyl and carbofuran on nematode populations below 10 grass cultivars. New Zealand Journal of Experimental Agriculture 11, 147-151.

Zhao, B. & Lin, F. (2005). Mutualistic symbiosis between *Bursaphelenchus xylophilus* and bacteria of the genus *Pseudomonas*. Forest Pathology. 35, 39-345.

Zhao, B. G., Liu, Y. & Lin, F (2007). Effects of bacteria associated with pine wood nematode *Bursaphelenchus xylophilus*) on development and egg production of the nematode. Journal of Phytopathology. 155, 26-30.

The invention claimed is:

1. A method of reducing losses in crop yield caused by infestation of crop growth media with plant pathogenic nematodes comprising the step of:

applying a composition comprising an active ingredient to the crop growth media and/or a plant being grown in the crop growth media in a crop growing area, the active ingredient being applied in an amount sufficient to reduce the losses in the crop yield, wherein the active ingredient consists of beta glucan and mannitol.

2. The method as claimed in claim 1, wherein the composition is applied in an amount such that greater than 60 grams/Hectare of the beta glucan and the mannitol is applied to the growing area.

3. The method as claimed in claim 2, wherein the composition is applied:

to the plant at root developmental stages, comprising one or more of: root primordium formation, root meristem formation, establishment of tissue systems, root elongation or root hair formation;

to the plant during tuber growth and developmental stages, comprising one or more of: sprout development, vegetative growth, tuber initiation, tuber growth or tuber maturation, wherein a first application of the composition is at 50% post-emergence followed by application at regular weekly intervals for a period of four to six weeks;

at regular intervals during key plant developmental stages;

at root and/or shoot emergence;

on a regular basis at a minimum rate of approximately 60 g/Hectare;

as a pre-sowing treatment, either to a seed prior to germination or to the seed post-germination and/or prior to the seed being sown;

in accordance with diversified germination behaviour of a seed population, with first fertirrigation or soil application taking place one week after sowing and at regular intervals subsequently thereafter, also by fertirrigation or soil application, with a total duration and timing of intervals dependent on life-cycle characteristics of the particular nematodes species targeted and root growth, vegetative growth and/or reproductive growth of the crop in use;

in accordance with the diversified germination behaviour of a seed population, with first foliar application taking place at 50% post-emergence, followed by applications whose total duration and timing depend on the life-cycle characteristics of the particular nematodes species targeted and the root growth, vegetative growth and/or reproductive growth of the crop in use;

to annual plants and/or their growth media at one or more time points including seed sowing, seed sowing to harvest, post harvest or pre-sowing;

to biennial plants and/or their growth media at time points throughout the two year life cycle;

to perennials and/or their growth media at one or more time points including pre-planting, planting, growing, blooming, seeding or post-harvest periods throughout a number of years;

to the plant and/or growth media at one or more time-points including prior to a growing season, during the growing season, at the end of the growing season, just after the growing season, or outside of the growing season, during a summer off-season period, during a winter off-season period or periods of crop rotation;

to the plant and/or growth media of cool season crops, cover crops or turf grass; or to the plant and/or growth media during processes of winter seeding, spring seeding, summer seeding, frost seeding, dormancy seeding or overseeding.

4. The method as claimed in claim 2, wherein the plants are selected from:

families of non-flowering, seed producing plants belonging to the Gymnospermae division;

families of flowering plants belonging to the Angiospermae division;

the Solanaceae family of flowering plants selected from potato (*Solanum tuberosum*), tomato (*Solanum lycopersicon*), pepper (*Capsicum* spp), eggplant (*Solanum melongena*), petunia (*Petunia hybrid*), tree tomato (*Cyphomandra betacea*), pepino (*Solanum muricatum*), naranjilla (*Solanum quitoense*) and coffee (*Coffea Arabica*);

the plant belongs to the Poaceae family of monocotyledonous flowering plants;

the plant belongs to the Brassicaceae family of flowering plants; or the plant belongs to the family Amaranthaceae family of flowering plants.

5. The method as claimed in claim 2, wherein enhanced growth is conferred in vegetative tissues or reproductive plant organs selected from root, rhizoid, stem, leaves, flower, seed, fruit, cones, strobili or spores.

6. The method as claimed in claim 2, wherein increments in growth, yield or marketable-grade of plants are achieved by enhancing tolerance to biotic stress and secondary diseases, altering food supply or favourably interfering with the nematode life-cycle, fecundity, development or digestive system in a direction of decreased pathogenicity.

7. The method as claimed in claim 2, wherein population dynamics and/or population density of free living nematodes are maintained and/or altered to levels which enhance the overall soil, soil ecosystem, soil fertility, levels of soil biota and microbiota and/or to levels which reduce numbers of other pathogens and/or pests.

8. The method as claimed in claim 7, wherein the free living nematodes are selected from parasitic species, beneficial bacteria/fungal feeders, colonizers or persisters.

9. The method as claimed in claim 7, wherein the microbiota are selected from bacteria or fungi species present on the free living nematodes, within the free living nematodes, within the soil ecosystem, on the plants, within the free living nematode intestinal tract, soil-derived gut bacteria, species which form part of nematode-bacterium symbioses, species present in eggs and/or cysts, species which form part of entomopathogenic nematode-bacterium complexes, species which influence nematode reproduction, nematophagous bacteria, rhizobacteria, endophytic fungi and soil bacteria or fungi which provide micro- and/or macro-nutrients in bioavailable forms.

10. The method as claimed in claim 2, wherein crop yield is enhanced in conditions known to otherwise negatively impact on the efficacy of commercial nematicides.

11. The method as claimed in claim 10, wherein conditions known to otherwise negatively impact on the efficacy of commercial nematicides include non-favorable weather or climatic conditions.

12. The method as claimed in claim 2, wherein the composition does not pose a danger to bees or harm bee populations.

13. The method as claimed in claim 1, wherein the composition is applied:

to the plant at root developmental stages, comprising one or more of: root primordium formation, root meristem formation, establishment of tissue systems, root elongation or root hair formation;

to the plant during tuber growth and developmental stages, comprising one or more of: sprout development, vegetative growth, tuber initiation, tuber growth or tuber maturation, wherein a first application of the composition is at 50% post-emergence followed by application at regular weekly intervals for a period of four to six weeks;

at regular intervals during key plant developmental stages;

at root and/or shoot emergence;

on a regular basis at a minimum rate of approximately 60 g/Hectare;

as a pre-sowing treatment, either to a seed prior to germination or to the seed post-germination and/or prior to the seed being sown;

in accordance with diversified germination behaviour of a seed population, with first fertirrigation or soil application taking place one week after sowing and at regular intervals subsequently thereafter, also by fertirrigation or soil application, with a total duration and timing of intervals dependent on life-cycle characteristics of the particular nematodes species targeted and root growth, vegetative growth and/or reproductive growth of the crop in use;

in accordance with the diversified germination behaviour of a seed population, with first foliar application taking place at 50% post-emergence, followed by applications whose total duration and timing depend on the life-cycle characteristics of the particular nematodes species targeted and the root growth, vegetative growth and/or reproductive growth of the crop in use;

to annual plants and/or their growth media at one or more time points including seed sowing, seed sowing to harvest, post harvest or pre-sowing;

to biennial plants and/or their growth media at time points throughout the two year life cycle;

to perennials and/or their growth media at one or more time points including pre-planting, planting, growing, blooming, seeding or post-harvest periods throughout a number of years;

to the plant and/or growth media at one or more time-points including prior to a growing season, during the growing season, at the end of the growing season, just after the growing season, outside of the growing season, during a summer off-season period, during a winter off-season period or periods of crop rotation;

to the plant and/or growth media of cool season crops, cover crops or turf grass; or to the plant and/or growth media during processes of winter seeding, spring seeding, summer seeding, frost seeding, dormancy seeding or overseeding.

14. The method as claimed in claim 1, wherein the plants are selected from:

families of non-flowering, seed producing plants belonging to the Gymnospermae division;

families of flowering plants belonging to the Angiospermae division;

the Solanaceae family of flowering plants selected from potato (*Solanum tuberosum*), tomato (*Solanum lycopersicon*), pepper (*Capsicum* spp), eggplant (*Solanum melongena*), petunia (*Petunia* hybrid), tree tomato (*Cy-*

*phomandra betacea*), pepino (*Solanum muricatum*), naranjilla (*Solanum quitoense*) and coffee (*Coffea Arabica*);

the plant belongs to the Poaceae family of monocotyledonous flowering plants;

the plant belongs to the Brassicaceae family of flowering plants; or the plant belongs to the family Amaranthaceae family of flowering plants.

15. The method as claimed in claim 1, wherein enhanced growth is conferred in vegetative tissues or reproductive plant organs selected from root, rhizoid, stem, leaves, flower, seed, fruit, cones, strobili or spores.

16. The method as claimed in claim 1, wherein increments in growth, yield or marketable-grade of plants are achieved by enhancing tolerance to biotic stress and secondary diseases, altering food supply or favourably interfering with the nematode life-cycle, fecundity, development or digestive system in a direction of decreased pathogenicity.

17. The method as claimed in claim 1, wherein population dynamics and/or population density of free living nematodes are maintained and/or altered to levels which enhance the overall soil, soil ecosystem, soil fertility, levels of soil biota and microbiota and/or to levels which reduce numbers of other pathogens and/or pests.

18. The method as claimed in claim 17, wherein the free living nematodes are selected from parasitic species, beneficial bacteria/fungal feeders, colonizers or persisters.

19. The method as claimed in claim 17, wherein the microbiota are selected from bacteria or fungi species present on the free living nematodes, within the free living nematodes, within the soil ecosystem, on the plants, within the free living nematode intestinal tract, soil-derived gut bacteria, species which form part of nematode-bacterium symbioses, species present in eggs and/or cysts, species which form part of entomopathogenic nematode-bacterium complexes, species which influence nematode reproduction, nematophagous bacteria, rhizobacteria, endophytic fungi and soil bacteria or fungi which provide micro- and/or macro-nutrients in bioavailable forms.

20. The method as claimed in claim 1, wherein crop yield is enhanced in conditions known to otherwise negatively impact on the efficacy of commercial nematicides.

21. The method as claimed in claim 20, wherein conditions known to otherwise negatively impact on the efficacy of commercial nematicides include non-favorable weather or climatic conditions.

22. The method as claimed in claim 1, wherein the composition does not pose a danger to bees or harm bee populations.

23. The method as claimed in claim 1, wherein the composition is applied in an amount such that greater than 60 grams/Hectare of the beta glucan or the mannitol is applied to the growing areas.

24. The method as claimed in claim 1, wherein the composition:
is non-nematicidal;
does not pose a risk to the ecosystem; and
does not pose a risk to an individual applying the composition, and wherein the composition reduces losses in crop yield.

* * * * *